US006432650B1

(12) United States Patent
Christian et al.

(10) Patent No.: US 6,432,650 B1
(45) Date of Patent: Aug. 13, 2002

(54) AMPLIFICATION OF CHROMOSOMAL DNA IN SITU

(75) Inventors: Allen T. Christian, Tracy; Matthew A. Coleman; James D. Tucker, both of Livermore, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/705,471

(22) Filed: Nov. 2, 2000

Related U.S. Application Data

(60) Provisional application No. 60/179,363, filed on Jan. 31, 2000.

(51) Int. Cl.$^7$ .............................. C12Q 1/68; C12P 19/34; C07H 21/04
(52) U.S. Cl. ...................... 435/6; 435/91.2; 536/24.33
(58) Field of Search ................... 435/6, 91.2; 536/24.33

(56) References Cited

U.S. PATENT DOCUMENTS

| | | | |
|---|---|---|---|
| 5,538,869 A | 7/1996 | Siciliano et al. | 435/91.2 |
| 5,545,524 A | 8/1996 | Trent et al. | 435/6 |
| 5,693,464 A | 12/1997 | Trent et al. | 435/6 |
| 5,814,444 A | 9/1998 | Rabinovitch | 435/6 |
| 5,856,089 A | 1/1999 | Wang et al. | 435/6 |

FOREIGN PATENT DOCUMENTS

| | | | |
|---|---|---|---|
| WO | WO 94/06816 | 3/1994 | C07H/21/04 |

OTHER PUBLICATIONS

Goldammer T et al. Generation of chromosome fragment specific bovine DNA by microdissection and DOP–PCR. Mammalian Genome, 7: 291–296, 1996.*
Gosden JR et al. Primed in situ DNA synthesis (PRINS). In PCR 3– a practical approach: PCR in situ hybridization. Oxford University Press Edition. p. 103–116, 1998.*
Engelen et al. A simple and efficient method for microdissection and microFISH. J.Med.Genet., 35: 265–268, 1998.*
Gosden JR et al. Primed in situ DNA synthesis (PRINS). In PCR 3–PCR in situ hybridization, a practical approach: Oxford University Press Edition, p. 103–116, 1998.*
de Fatima Bonaldo, M., "Normalization and Substraction: Two Approaches to Facilitate Gene Discovery", Genome Research, 6:791–806 (1996).
Christian, A., et al., "PCR in Situ Followed by Microdissection Allows Whole Chromosome Painting Probes to be Made From Single Microdissected Chromosomes", Mammalian Genome 10:628–631 (1999).
Gracia, E., et al., "Isolation of Chromosome–Specific ESTs by Microdissection–Mediated cDNA Capture", Genome Research, 7:100–107 (1997).
Gracia, E., et al., "Isolation of Genes Amplified in Human Cancers by Microdissection Mediated cDNA Capture", Human Molecular Genetics 5: (5)595–600 (1996).
Hozier, J. et al., "Preparative in Situ Hybridization: Selection of Chromosome Region–Specific Libraries on Mitotic Chromosomes", Genomics 19:441–447 (1994).
Kallioniemi, A., et al., "Comparative Genomic Hybridization for Molecular Cytogenetic Analysis of Solid Tumors", Science 258:818–821 (1992).
Meltzer, P., et al., "Identification of Region Specific Genes by Chromosome Microdissection" Cancer Genet Cytogenet 93:29–32 (1997).
Tirkkonen, M., et al., "Molecular Cytogenetics of Primary Breast Cancer by CGH", Genes, Chromosomes & Cancer 21:177–184 (1998).

* cited by examiner

Primary Examiner—Eggerton A. Campbell
Assistant Examiner—Suryaprabha Chunduru
(74) Attorney, Agent, or Firm—Ann M. Lee; Alan H. Thompson

(57) ABSTRACT

Amplification of chromosomal DNA in situ to increase the amount of DNA associated with a chromosome or chromosome region is described. The amplification of chromosomal DNA in situ provides for the synthesis of Fluorescence in situ Hybridization (FISH) painting probes from single dissected chromosome fragments, the production of cDNA libraries from low copy mRNAs and improved in Comparative Genomic Hybridization (CGH) procedures.

69 Claims, 3 Drawing Sheets

ATTACHMENT II (A) NEITHER GAIN NOR LOSS OF DNA
(B) GAIN OF AN ENTIRE CHROMOSOME
(C) LOSS OF AN ENTIRE CHROMOSOME
(D) GAIN OF ONE REGION AND LOSS OF ANOTHER

AMPLIFICATION OF CHROMOSOMAL DNA IN SITU

RELATED APPLICATION

This application claims the benefit under 35 U.S.C. §119 (e) of United States provisional patent application No. 60/179,363, filed Jan. 31, 2000, which is hereby incorporated by reference in its entirety.

The United States Government has rights in this invention pursuant to Contract No. W-7405-ENG-48 between the U.S. Department of Energy and the University of California, for the operation of Lawrence Livermore National Laboratory.

FIELD OF THE INVENTION

This invention relates to the amplification of chromosomal DNA in situ. In particular, this invention relates to the amplification of chromosomal DNA in situ prior to microdissection.

BACKGROUND OF THE INVENTION

Chromosome microdissection is an extremely useful molecular cytogenetic tool for the characterization and analysis of chromosomes. For example, microdissection has become a very popular method for making both whole-chromosome and region-specific painting probes for use in Fluorescence in situ Hybridization (FISH). In addition, microdissection has been applied to the isolation and characterization of region specific cDNAs.

While useful, microdissection does possess serious drawbacks, however. For instance, it is generally necessary to dissect multiple copies of a target chromosome or chromosome region to produce a probe sufficiently complex for FISH. Although band-specific probes have been made from single chromosome fragments, painting regions larger than this requires as many as 50 chromosome copies to be dissected for sufficient probe coverage. The need to dissect more than one copy of a target chromosome complicates the process of microdissection as it can be difficult to precisely locate the same chromosomal region when making multiple scrapes of a single band. As a result, the painting probe covers a wider region than desired. When probes are made for adjacent bands this can result in overlapping signals, which complicates analysis. Thus, the ability to make chromosome paints from single scrapes of a band, arm, or chromosome is highly desirable.

There is thus a need to amplify chromosomal DNA in situ in order to increase the amount of DNA associated with a chromosome or chromosome region to facilitate chromosome analysis by microdissection.

SUMMARY OF THE INVENTION

In order to meet these needs, the present invention is directed to the amplification of chromosomal DNA in situ to increase the amount of DNA associated with a chromosome or chromosome region. The chromosomes may be isolated from any chromosome-containing organism including birds (avian), reptiles, amphibians, plants, and mammals such as humans, mice and rats, etc. The chromosomes include mini chromosomes.

The amplification of chromosomal DNA in situ allows Fluorescence in situ Hybridization (FISH) painting probes to be made from single dissected chromosome fragments. Furthermore, the amplification of chromosomal DNA in situ permits the synthesis of cDNA libraries from low copy mRNAs. The amplification of chromosomal DNA in situ facilitates comparative hybridization and microdissection of tumor sections. In addition, the hybridization of cDNA libraries to chromosomes normalizes the frequency of the constituent cDNA sequences, i.e. increases the ratio of the less prevalent to more prevalent expressed sequences.

The present invention is directed to a method of preparing chromosomes for microdissection, comprising the steps of: a) fixing cells on a surface wherein the cells comprise chromosomes and the chromosomes include chromosomal DNA and b) amplifying the chromosomal DNA on the surface. The chromosomal DNA may be amplified by PCR including DOP-PCR.

The present invention is further directed to a method of microdissecting chromosomes, comprising the steps of: a) fixing cells on a surface wherein the cells comprise chromosomes and the chromosomes include DNA; b) amplifying the DNA in situ, and c) microdissecting the chromosomes. The DNA may be amplified by PCR including DOP-PCR in step b).

The present invention is further directed to a method of amplifying chromosomal DNA in situ, comprising the steps of: a) fixing cells on a surface wherein the cells comprise chromosomes and the chromosomes include DNA; b) preparing a PCR reaction buffer; c) adding the PCR reaction buffer to the fixed cells of step a); and d) amplifying the DNA by PCR in situ. The PCR amplification step d) may be DOP-PCR. The PCR reaction buffer will include DNA polymerase, eg. thermostable DNA polymerase.

The present invention is further directed to a method of amplifying chromosomal DNA in situ, comprising: a) providing cells embedded in paraffin wherein the cells comprise chromosomes and the chromosomes include DNA; b) preparing a PCR reaction buffer; c) combining the PCR reaction buffer with the paraffin embedded cells of step a) and d) amplifying the DNA by PCR in situ. The DNA in step d) may be amplified by DOP-PCR. This method may be used in comparative genomic hybridization (CGH) to compare the DNA content of cells, e.g. cancer cells vs. normal cells. For example, after DNA amplification in situ, CGH may be used on DNA isolated from tumor cells labeled with a fluorochrome of one color (e.g., green), and DNA from normal cells, usually but not necessarily obtained from a non-neoplastic region adjacent to the tumor, labeled with a different color (e.g., red). After hybridizing and washing steps, the chromosomes are analyzed for differential hybridization to compare and contrast cancerous and non-cancerous cells.

The present invention is further directed to a method of generating chromosome region-specific nucleic acids for a chromosomal region of interest comprising the steps of: a) obtaining chromosomes containing chromosomal DNA; b) amplifying the chromosomal DNA in situ, and c) microdissecting the chromosomal region of interest to provide a microdissected chromosome fragment containing microdissected chromosomal DNA. The amplification step b) may further comprise a polymerase chain reaction. The method may further comprise step e) labeling the amplified microdissected chromosomal DNA. The invention is further directed to labeled chromosomes and chromosome probes, and labeled chromosome region-specific nucleic acids for a chromosome region-specific nucleic acid produced by the method of the invention.

The DNA may be labeled using any conventional techniques, which permit detection. Examples of suitable labels include biotin-avidin immunofluorescent, digoxigenin, chromogenic, and radioisotopic labels and direct chemical labeling with fluorochromes.

The present invention is further directed to a method of localizing a chromosomal region of interest in a chromosome sample having nucleic acid sequences, comprising the steps of: a) providing a chromosome region-specific probe generated by: (i) amplifying the chromosomal DNA in situ, (ii) microdissecting the chromosomal region of interest to provide a microdissected chromosome fragment; (iii) amplifying the microdissected chromosome fragment; and (iv) labeling the amplified fragment to provide the probe; and b) contacting the chromosome sample with the probe under conditions favorable for hybridization between the probe and complementary nucleic acid sequences in the sample and c) determining the existence and location of hybridization in the chromosome sample.

The present invention is further directed to a method of screening a library of nucleic acid clones for a clone of a chromosomal region of interest comprising the steps of: a) providing a chromosome region-specific probe generated by: (i) amplifying the chromosomal DNA in situ, (ii) microdissecting the chromosomal region of interest to provide a microdissected chromosome fragment; (iii) amplifying the microdissected chromosome fragment; and (iv) labeling the amplified fragment to provide the probe; b) providing the library of clones to be screened; c) contacting each clone with the probe under conditions favorable for nucleic acid hybridization; and d) determining whether and in which clone hybridization has occurred.

The present invention is further directed to a method of amplifying a cDNA library, comprising: a) fixing cells on a surface wherein the cells comprise chromosomes and the chromosomes include genomic DNA; b) amplifying the genomic DNA on the surface to form amplified genomic DNA; c) hybridizing the cDNA library to the genomic DNA to form DNA hybrids; and d) amplifying the DNA hybrids on the surface to form an amplified cDNA library. In the method, the DNA in steps b) and d) may be amplified by PCR; e.g. DOP-PCR. The method may also include the additional step e) microdissecting the chromosomes and/or step f) amplifying the DNA hybrid from the microdissected chromosomes.

The present invention is further directed to a method of preparing a cDNA library specific to a particular chromosome region, comprising: a) fixing chromosomes including a chromosome region on a surface wherein the chromosomes include genomic DNA; b) amplifying the genomic DNA in situ to form amplified genomic DNA; c) hybridizing the cDNA library to the genomic DNA to form DNA hybrids; d) amplifying the DNA hybrids on the surface to form an amplified cDNA library; e) microdissecting the chromosome region wherein the chromosome region includes a portion of the amplified cDNA library; and f) amplifying the portion of the cDNA library. In the method, the amplification steps d) and f) may be with PCR primers specific for the cDNA library.

The present invention is further directed to a method of identifying expressed genes, comprising: a) fixing cells on a surface wherein the cells comprise chromosomes and the chromosomes include genomic DNA; b) amplifying the genomic DNA on the surface to form amplified genomic DNA; c) hybridizing the cDNA library to the genomic DNA to form DNA hybrids; d) amplifying the DNA hybrids on the surface to form an amplified cDNA library; and e) sequencing members of the amplified cDNA library to identify the expressed genes. In the method, the amplifications of steps b) and d) may be by PCR with primers specific for the cDNA library.

This invention is further directed to method of normalizing a cDNA library, comprising: a) fixing cells on a surface wherein the cells comprise chromosomes and the chromosomes include genomic DNA; b) amplifying said genomic DNA on said surface to form amplified genomic DNA; c) hybridizing the cDNA library to the amplified genomic DNA to form DNA hybrids; d) amplifying the DNA hybrids on the surface to form an amplified cDNA library; e) microdissecting the chromosomes including the amplified cDNA library; and f) amplifying the amplified cDNA library to form a normalized cDNA library.

BRIEF DESCRIPTION OF THE DRAWINGS

The invention will be better understood by reference to the following Figures in which.

DETAILED DESCRIPTION OF THE INVENTION

Figure 1:
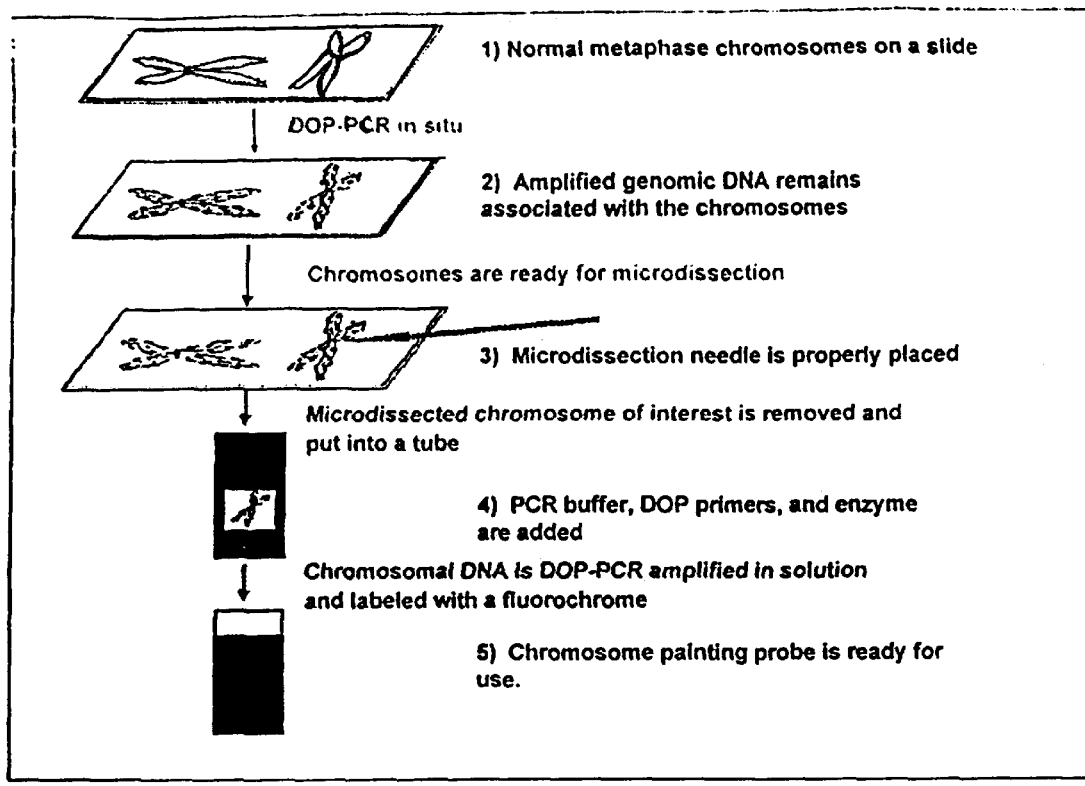
FIG. 1 shows a schematic diagram of DNA amplification in situ and the use of DNA amplification in situ in the preparation of chromosome paints.

In order to more fully understand the invention, the following definitions are provided.

Polymerase Chain Reaction (PCR): The polymerase chain reaction (PCR) is a technique utilized to amplify DNA. Typical PCR reactions include appropriate PCR buffers, DNA polymerase and one or more oligonucleotide primers. Various modifications of PCR techniques are possible as detailed in *Current Protocols in Molecular Biology* ed. F. M. Ausubel, R. Brent, D. D. Moore, K. Struhle, Massachusetts General Hospital and Harvard Medical School. (1987) which is hereby incorporated by reference.

Oligonucleotide Primers: Oligonucleotide primers are short chains of nucleotides useful in PCR techniques, DNA sequencing and cloning methods. Oligonucleotide primers include degenerate oligonucleotide primers (DOP) such as CCGACTCGAGNNNNNNATGTGG (SEQ ID NO1[1]) where NNNNNN represents the degenerate sequence. The degenerate sequence contains a mixture of DNA sequences rather than just one DNA sequence. "N" represents the four possible nucleotides in the DNA sequence: "A", "T", "C" and "G" for Adenine, Thymine, Cytosine and Guanine, respectively. As such, the degenerate probe sequences contain mixtures of various probes including all possible combinations of A, T, C and G at the "N" positions.

DOP PCR: DOP PCR is Degenerate Oligonucleotide Primer Polymerase Chain Reaction. DOP PCR is performed with degenerate oligonucleotide primers. DOP PCR may be performed in situ as described herein. DOP-PCR is described in detail in Telenius, H., et al. Genomics 18:718–725 (1982) which is hereby incorporated by reference.

PCR In situ: PCR in situ is similar to conventional PCR except that PCR reaction mix is added to a chromosome template on a surfaces such as a microscope slide or to a formalin-fixed paraffin-embedded tissue section rather than in a microfuge tube. With PCR in situ, the PCR products remain closely associated with their target sequences. The reaction products can be identified, if necessary, by incorporating a dNTP-conjugated fluorochrome to the PCR solution. By performing PCR such as DOP PCR on chromosomes or tissue sections prior to microdissection, sufficient DNA amplification occurs in situ to permit single chromosomes to serve as templates for subsequent PCR amplifications in a microfuge tube.

Microdissection: Microdissection is a technique in which a micromanipulator and a glass needle are used to selectively remove from a surface, e.g. a slide, a small group of cells, a single cell, a chromosome or chromosome region.

HeadStart Microdissection: HeadStart microdissection is the performance of PCR in situ on intact chromosomes to amplify chromosomal DNA and thereby increase the amount of DNA associated with a chromosome or chromosome region prior to microdissection. This technique allows consistent and reliable production of whole chromosome painting probes from single microdissected chromosomes and chromosome regions for use in FISH and for the production of cDNA libraries from chromosomes and chromosome fragments.

FISH: Fluorescence In situ Hybridization (FISH) is a procedure utilized to visualize chromosomes and chromosome regions via the use fluorescent DNA probes.

WCP: Whole Chromosome Probes (WCP) are FISH probes for whole chromosomes.

CAP: Chromosome-arm painting probes (CAP) are FISH probes for chromosome arms.

Gene Recovery Microdissection (GRM): Gene Recovery Microdissection (GRM) is a procedure to isolate cDNA (copy DNA) from metaphase chromosomes which enables the creation of gene expression libraries from specific chromosome regions. cDNA is a DNA copy of the messenger RNA expressed by a cell. Genes are said to be expressed when a mRNA is transcribed from a particular gene.

Comparative Genomic Hybridization (CGH): Comparative Genomic Hybridization (CGH) is a technique used to compare the DNA content of cells, e.g. cancer cells vs. normal cells. For example, CGH may be used on DNA isolated from tumor cells labeled with a fluorochrome of one color (eg., green), and DNA from normal cells, usually but not necessarily obtained from a non-neoplastic region adjacent to the tumor, labeled with a different color (eg., red). After hybridizing and washing steps, the chromosomes are analyzed for differential hybridization to compare and contrast cancerous and non-cancerous cells.

Taking into account these definitions, the present invention is directed to methods of amplification of chromosomal DNA in situ and the use of the in situ amplified DNA in chromosomal analysis.

1. Cell Fixation

As a first step in the process of amplifying DNA in situ, cells and chromosomes are fixed to solid surfaces such as a microscope slide cover slip by procedures well known in art. Whole blood is cultured generally for 48 h after which Colcemid is added to arrest the cells in metaphase. Colcemid disrupts the mitotic spindle causing the cells to stop cycling in metaphase. The cultures are then harvested 4 h later by treatment with hypotonic solution such as KCl followed by three fixations in methanol:acetic acid (3:1 v/v). The fixed cells are then dropped onto a solid surface such as 24×60 mm coverslips where they are air dried and stored at room temperature. The fixed cells are generally used within 24 hours of fixation in the procedures of this invention.

2. Chromosomal DNA Amplification In situ

Figure 2:
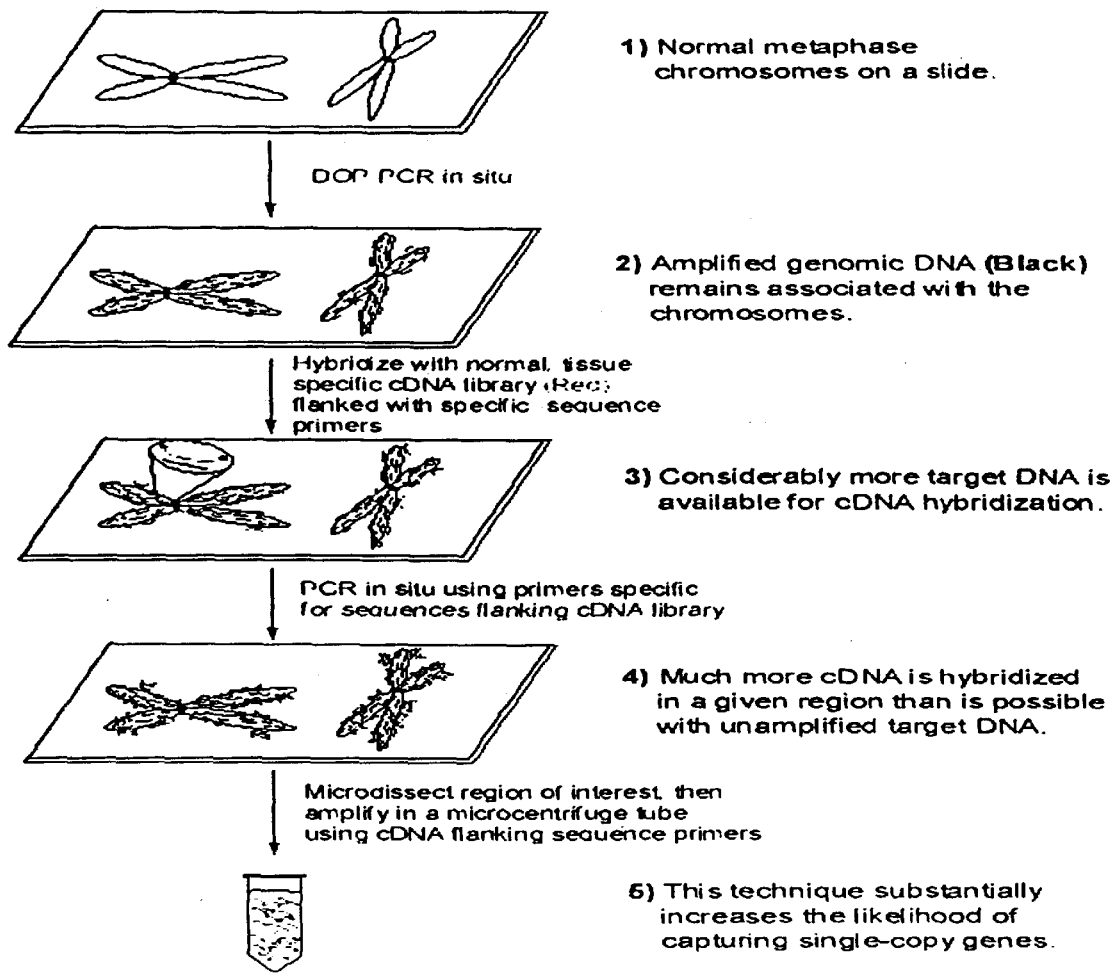
FIG. 2 shows a schematic diagram illustrating the steps involved in making chromosome-region specific cDNA libraries using Gene Recovery Microdissection.

Chromosomal DNA Amplification In situ is illustrated in FIGS. 1 and 2. Metaphase cells are fixed to a surface such as a glass slide or a cover slip as described above. PCR reaction buffers are prepared and added to the fixed cells. The fixed metaphase cells are then subject to in situ PCR to amplify the chromosomal (target DNA) on the slide.

DNA amplification buffers are prepared for chromosomal DNA amplification in situ by procedures well known in the art. The amplification buffers contain DNA polymerase, reaction buffer, dATP, dTTP, dCTP, and dGTP (e.g., Boehringer Mannheim, Indianapolis, Ind.), and a suitable primer such as DOP primer (5'-CGACTCGAGNNNNNNATGTGG-3') SEQ ID NO:1. While DOP primers are preferred, any random primer or primers capable of amplifying the genomic DNA will suffice. In addition, while thermostable DNA polymerases are preferred for the reaction any DNA polymerase will suffice.

The amplification buffer is then placed on microscope slides. Next, a coverslip containing fixed cells is inverted and gently placed on the slide so that the cells are in contact with the amplification buffer. The coverslip is sealed to the microscope slide with a sealant such as rubber cement, Vaseline®, nail polish or other substances that will minimize the evaporation of moisture between the surfaces.

PCR reactions are performed using a PCR thermocycler such as a DNA Engine Thermocycler (MJR Research Inc., Watertown, Mass.). The thermal profile is designed to maximize the amplification of the chromosomal DNA while minimizing diffusion of PCR products from the chromosomal region from which they were derived. A suitable thermal profile includes: 95° C. for 10 min, 8 cycles at 94° C. for 1 min, 30° C. for 5 min, and a ramp of 0.1° C./s up to 65° C. for 5 min, 12 cycles at 94° C. for 1 min, 56° C. for 5 min, and 72° C. for 5 min, followed by 72° C. for 5 min and held at 4° C. until removed.

Variations in the slope of the ramp, the number of low and high temperature cycles and the primer annealing temperature have all been attempted, and do not seem to affect the outcome in any significant way.

Once the thermal cycle is complete, the coverslips are removed from the slide and soaked in a solution such as water or 4×SSC/0.1% triton solution for 5 min at room temperature.

3. Production of Chromosome Paints

The production of chromosome paints by amplification of DNA in situ is illustrated in FIG. 1. Metaphase cells are fixed to the surface as described above. In step 1, fixed metaphase cells undergo in situ PCR to amplify the chromosomal (target) DNA on the slides. DNA amplification may be with DOP primers. Next, a microdissection needle is used to remove the chromosome of interest from the slide. The dissected chromosome is placed in a tube containing buffer, primer and enzyme and the DNA is amplified and labeled. The chromosome painting probe is then ready for use.

The chromosome paint probes of the invention can be labeled using any conventional techniques and labels, which permit detection. Examples of suitable labels include biotin-avidin, immunofluorescent labels, digoxigenin, chromogenic, and radioisotopic labels and direct chemical labeling with fluorochromes. The probes may be used to label whole chromosomes or partial chromosomes.

Two coverslips or other solid surfaces are generally used for DNA amplification, e.g. DOP-PCR in situ; one is used as a positive control by incorporating rhodamine-6-dUTP or other suitable detection agent and the other is used for microdissection.

DNA amplification in situ is generally performed with PCR and suitable primers. For example, fifty-$\mu$l reaction drops containing 5 $\mu$l DNA Polymerase such as Thermo Sequenase DNA Polymerase, 5 $\mu$l polymerase reaction buffer such as Thermo Sequenase reaction buffer, 200 $\mu$M of each dATP, dTTP, dCTP, and 4 $\mu$M primer such as a DOP primer (5'-CCGACTCGAGNNNNNNATGTGG-3') SEQ ID NO:1 are placed on unfrosted microscope slides. Next, a coverslip containing fixed cells is inverted and gently placed on the slide so that the cells are in contact with the solution. Rubber cement or other suitable sealant is used to seal the coverslip to the microscope slide.

The thermal profile is designed to maximize the amplification of the chromosomal DNA while minimizing diffusion of PCR products from the chromosomal region from which they were derived. A suitable thermal profile includes 95° C. for 10 min, 8 cycles at 94° C. for 1 min, 30° C. for 5 min, and a ramp of 0.1° C./s up to 65° C. for 5 min, 12 cycles at 94° C. for 1 min, 56° C. for 5 min, and 72° C. for 5 min, followed by 72° C. for 5 min and held at 4° C. until removed. ThermoSequenase is preferred because of its stability at high temperatures; new polymerase need not be added following each cycle. Other suitable profiles include variations in time and number of cycles, and slight variations in temperatures. The number of cycles directly affects product length and are thus predicated upon the desired outcome. Temperature profiles are determined strictly by thermodynamics. Different primers have different binding energies, and the desired specificity also plays a role. In this case, the first ~8 cycles are done with minimal specificity; thus, the annealing temperature is very low. Subsequent cycles are done with a high desired specificity, requiring a higher annealing temperature. These temperatures can be varied some, but the reaction becomes less and less efficient as the deviation from perfection increases.

Positive control DOP-PCR in situ experiments will generally include 40 $\mu$M tetramethylrhodamine-6-dUTP added to the reaction in addition to the components listed above. All PCR reactions are performed using a thermocycler such as a DNA Engine thermocycler (MJR Research Inc., Watertown, Mass.). The positive control slide indicates whether or not the reaction worked.

The control reaction is mounted onto a microscope slide using, for example 0.1 $\mu$g/ml of 4',6-diamidino-2-phenylindole (DAPI) and an antifade solution. Metaphase spreads may be visualized using a Zeiss Axioskop (Carl Zeiss, Inc, Thornwood, N.Y.) and images may be captured by a Vysis QUIPS Imaging Analysis System (Vysis, Downers Grove, Ill.). The PCR is generally considered successful if all chromosomes in a metaphase spread are labeled with the fluorochrome.

Chromosome paints are not made from the positive control slides. Instead, the paints are made from replicate slides that did not include a fluorochrome (e.g. rhodamine) in the reaction mixture. Once complete, the coverslips are removed from the slide and soaked in a 4×SSC/0.1% triton solution or other suitable solution for 5 min at room temperature.

The unlabeled coverslip is removed from the SSC solution, rinsed with water to remove any citrate (which inhibits PCR reactions by chelating the cofactor magnesium), blown dry, and used for microdissection. Appropriately sized glass needles are made using a Flaming/Brown Micropipette Puller (Sutter Instrument Co., Novato, Calif.), a Nikon Phase Contrast Microscope (Nikon Instruments Co., Melville, N.Y.) and a Narashige micromanipulator. One copy of the desired chromosome, arm or region is microdissected and placed in a 500 $\mu$l microfuge tube. The DNA is then amplified by PCR, for example, in a 15 $\mu$l reaction drop containing 1.5 $\mu$l Thermo Sequenase DNA Polymerase, 1.5 $\mu$l Thermo Sequenase reaction buffer, 200 $\mu$M of each dATP, dGTP, dCTP, and dGTP, and 4 $\mu$M DOP primer. Thirty $\mu$l of mineral oil are added to the reaction mixture to prevent evaporation.

The thermal profile is designed to maximize the amplification of the chromosomal DNA. For example, a suitable thermal profile is 95° C. for 10 min, 6 cycles of 94° C. for 1 min, 30° C. for 2 min, and a ramp of 1° C./s up to 65° C. for 3 min, 30 cycles of 94° C. for 1 min, 56° C. for 1 min, and 72° C. for 3 min, followed by a single 72° C. for 5 min and held at 4° C. until removed.

To verify that DNA amplification has occurred, each sample is electrophoresed, for example, on a 1.5% agarose gel at 100 V for 1 h. If appropriately-sized products (300–600 base pairs) are identified, a fluorochrome is incorporated in a second generation PCR using 2 $\mu$l of the first generation product as a template.

The 50 $\mu$l labeling reaction may contain 20 U of DNA polymerase such as Thermo Sequenase DNA Polymerase, 26 mM Tris-HCl, pH 9.0, 6.5 mM MgCl$_2$, 200 $\mu$M of each dATP, dTTP, dCTP, and dGTP, 40 $\mu$M Rhodamine-6-dUTP, and 4 $\mu$M primer such as DOP primer (5'-CCGACTCGAGNNNNNNATGTGG-3') SEQ ID NO:1.

The painting probe is added to a hybridization mix, e.g. 50% formamide, 2×SSC, 10% dextran sulfate, and 3 μg of blocking DNA to a final volume of 15 μl. In the case of the rat, total genomic DNA may be used as the blocking DNA, and CoT-1 DNA (Life Technologies, Gaithersburg, Md.) is used for the human hybridizations. Metaphase spreads are denatured in 70% formamide/2×SSC, pH 7.0 for 3 min followed by successive washes in 70%, 85% and 100% ethanol for 3 minutes each. The probe mixture is denatured at 70° C. for 5 min and applied to the denatured slides, covered with 22×22 mm coverslips, sealed with rubber cement and hybridized overnight at 37° C. in a 5% $CO_2$ atmosphere.

Following hybridization, unbound probe is removed by washing, for example with three 5-minute washes in 50% formamide, 2×SSC, pH 7.0 (45° C.), followed by one 5-minute wash in 2×SSC (45° C.) and one 5-min wash in 2×SSC with 1% Triton-X (45° C.). The metaphase chromosomes are then counterstained with DAPI and an antifade solution. Metaphase spreads are observed using a Zeiss Axioskop fluorescence microscope with a dual band-pass filter for Rhodamine and DAPI (Chroma Technology Corp, Brattleboro, Vt.) and images captured by a Vysis QUIPS Imaging Analysis System (Vysis, Downers Grove, Ill.).

The chromosome paints have various uses in chromosome analysis. Chromosome translocations or movement of chromosomal regions can be studied and analyzed using the paints of the invention. Furthermore, these paints find use in disease analysis and chromosome characerization.

4. cDNA Libraries

Gene Recovery Microdissection (GRM) is a means for creating a chromosome region-specific cDNA library for any species, tissue and cell type from a single microdissected normal metaphase chromosome, eliminating the need to dissect multiple copies of the target. The process involves hybridizing a cDNA library specific for the species, tissue and cell type of interest onto DOP-PCR amplified metaphase chromosomes. This step also normalizes the library, increasing the ratio of less prevalent to more prevalent expressed genes. PCR is used again to amplify the cDNA molecules in situ following hybridization, and the desired chromosome regions are isolated by microdissection. The cDNA molecules hybridized to the dissected genomic DNA are then amplified by PCR in a tube by using primers specific for the linker arms on the cDNA. The cDNA molecules are then cloned and sequenced. In situ amplification followed by microdissection allows complex libraries to be made from single microdissected chromosomes and chromosome regions, possibly by increasing both the number of targets for in situ hybridization and probe accessibility to the target chromosomes.

The Gene Discovery Microdissection process is illustrated in FIG. 2. cDNA libraries are constructed for a tissue of interest; the end result is a library with a median size of approximately 800–1200 base pairs with linker sequences attached to each end. Prior to hybridizing the cDNA to metaphase spreads, the spreads undergo extensive preparation. Metaphase cells are fixed to a surface as described above. Fixed metaphase cells first undergo in situ DOP-PCR (Step 1) to amplify the chromosomal (target) DNA on the slides. Following washing to remove nonspecifically bound DNA, the slides are crosslinked in a Stratalinker 1800 (Stratagene, LaJolla, Calif.), to preclude PCR amplification of the genomic DNA. Next, the cDNA library is hybridized to these cells (Step 2). This hybridized library is amplified in situ using primers specific for the flanking linkers used in the library synthesis (Step 3). The genomic regions of interest containing the hybridized cDNA are microdissected and the individual dissected fragments are placed in microcentrifuge tubes, and the cDNA molecules are amplified again with the linker-primed PCR (Step 4). The resulting chromosome-region specific cDNA libraries may then be sequenced.

Three steps in the cDNA library preparation procedure shown in FIG. 2 are important to emphasize. The first is the amplification of the target sequences, shown in Step 2. This results in considerably more targets for hybridization in any given genomic region; as a result, only one chromosome needs to be dissected to achieve a complex expression library. Second is the hybridization shown in Step 3. This normalizes the expression library, making it more likely that all of the expressed genes in the region will be represented in the final library. Third is the cDNA amplification shown in Step 4. This increases the likelihood that all of the hybridized sequences will be amplified and cloned.

a. Library Normalization

The expression libraries produced using GRM are normalized as a byproduct of the hybridization procedure; this provides a significant increased probability of obtaining a complete expression library for a given region. The importance of library normalization is especially critical in the case of EST library construction. There are three classes of mRNA in a cell as defined by reannealing kinetics: superprevalent, in which 10–15 mRNA sequences comprise as much as 20% of the total mRNA in a cell; intermediate, comprising ~40% of the mRNA total from as many as 2000 types of sequence; and complex, in which the last 40% of the mRNA in a cell is made up of approximately 20,000 mRNA's. In a non-normalized library, the probability of picking a clone containing one of the unique sequences in the complex group is estimated to be as low as $1\times10^{-7}$. This results in a redundancy level (in which the same sequence is isolated repeatedly) of greater than 60%. In a normalized library, the superprevalent, intermediate and complex populations are present in near equal percentages; the likelihood of picking a superprevalent sequence is within an order of magnitude of picking a complex mRNA.

Library normalization is accomplished through the hybridization step. Annealing to genomic DNA targets results in saturation of the target by the cDNA probe; regardless of the excess of certain sequences in a probe complement, only the number of probe molecules corresponding to the number of target sites will be included in the final library. The pre- and post-hybrizations are designed to produce more target and a greater number of normalized cDNA sequences, respectively. Although a perfectly normalized library is nearly impossible to produce, those made with GRM are much more likely to contain all three subpopulations of mRNA in reasonably equal proportion as compared to un-normalized libraries.

b. cDNA Library Construction

Messenger RNA is isolated from appropriate tissue or cells using an mRNA isolation kit such as the Ambion Poly(A)Pure mRNA isolation kit (Catalog #1915, Ambion Inc., Austin, Tex.). First strand cDNA synthesis is done using a kit, e.g. the Amersham cDNA synthesis module (Catalog #RPN1256, Amersham Life Science, Buckinghamshire, England). The first strand primer is a modified version of the Life Technologies (Life Technologies, Gaithersburg, Md.) 3' RACE (Rapid Amplification of cDNA Ends) primer, with the addition of a random dATP, dGTP or dCTP on the 3' end to serve as an anchor as represented by the following primers: GGCCACGCGTCGACTAGTACTTTTTTTTTTTTTTTA (SEQ ID NO:2); GGCCACGCGTCGACTAGTACTTTTTTTTTTTTTTTC (SEQ ID NO:3) and GGCCACGCGTCGACTAGTACTTTTTTTTTTTTTTTG (SEQ ID NO:4).

First strand synthesis time is generally 1 hour for the 'full length' first strand to be used to make the 5'-rich library for protein homology screening, or is cut to 10 minutes to provide a shorter library comprised primarily of the 3' ends of the mRNA for EST screening. Full length cDNAs are too long for optimal hybridization because of the steric hindrance caused by the cDNA itself. The samples are treated with RNase H per the Amersham kit, and a poly dC tail is added using terminal transferase. In the case of the shorter 3' library, 20 cycles of PCR are done using the Life Technologies Abridged Universal Amplification Primer [(AUAP, 20 nM,) GGCCACGCGTCGACTAGTAC)], SEQ ID NO:5, 5 µl Thermo Sequenase DNA Polymerase, 5 µl Thermo Sequenase reaction buffer, 200 µM of each dATP, dGTP, dCTP, and dGTP in a 50 µl reaction volume. The thermal profile was selected to optimize cDNA synthesis. A suitable profile consists of 95° C. for 10 min, 20 cycles of 94° C. for 1 min, 56° C. for 1 min, and 72° C. for 3 min, followed by a single 72° C. for 5 min and incubation at 4° C. until removed.

To make the 5'-rich library, a second strand synthesis is done using the same reaction mixture as used in the 20-cycle PCR described above, but for one 10-minute extension. The entire process described above is then performed, starting with the poly dC tail addition, and followed by the 20 cycle PCR reaction using the AUAP primer. The result of this procedure is two cDNA libraries, one containing the 3' mRNA sequences and the other containing the 5' mRNA sequences. These two libraries are co-hybridized for the GRM procedure, and result in a PCR-amplifiable product that covers the greatest possible amount of transcribed sequence.

c. Gene Recovery cDNA Microdissection

Gene Recovery cDNA microdissection is carried out as follows. Fifty-µl reaction drops containing 5 µl DNA polymerase, e.g. Thermo Sequenase DNA Polymerase, 5 µl Thermo Sequenase reaction buffer (Amersham, Arlington Heights, Ill.), 200 µM of each dATP, dTTP, dCTP, and dGTP, and 4 µM DOP primer (5'-CCGACTCGAGNNNNNNATGTGG-3') SEQ ID NO:1 are placed on unfrosted microscope slides. Next, a coverslip with fixed cells is inverted and gently placed on the slide so that the cells are in contact with the solution. Rubber cement or other suitable sealant is used to seal the coverslip to the microscope slide.

All PCR reactions are performed using a thermocycler such as a DNA Engine thermocycler (MJR Research Inc., Watertown, Mass.). A suitable thermal profile consists of 95° C. for 10 min, 8 cycles at 94° C. for 1 min, 30° C. for 5 min, and a ramp of 0.1° C./s up to 65° C. for 5 min, 12 cycles at 94° C. for 1 min, 56° C. for 5 min, and 72° C. for 5 min, followed by 72° C. for 5 min and held at 4° C. until removed.

Once complete, the coverslips are removed from the slide and soaked in a 4×SSC/0.1% triton solution for 5 min at room temperature. The coverslips are then put into a 254 nm UV Stralinker for 15 minutes. This treatment with 254 nm light has no effect on cDNA/genomic DNA hybridization, but greatly reduces the possibility of amplifying genomic DNA as compared to cDNA by formation of a DNA dimer in a small region of the DNA. Dimerization will prevent DNA polymerase from synthesizing a complementary strand of the genomic DNA because the polymerase cannot run along the dimerized (damage) strand. However, dimerization will not prevent a cDNA from hybridizing to its complementary genomic DNA. In addition to treatment with 254 nm light, genomic DNA may be treated with chemical cross linkers such as cisplatin, ionizing radiation or chemicals to induce dimerization.

Metaphase spreads on the coverslip are then denatured for example by treatment with 70% formamide/2×SSC, pH 7.0 for 3 min followed by successive washes in 70%, 85% and 100% ethanol for 3 minutes each.

A 40 µ reaction mix containing 50% formamide, 2×SSC, 10% dextran Sulfate and 500 ng cDNA is denatured at 70° C. for 5 min and applied to a clean slide, covered with the denatured coverslips, sealed with rubber cement and hybridized overnight at 37° C. in a 5% $CO_2$ atmosphere. Following hybridization, unbound probe is removed with three 5-min washes in 50% formamide, 2×SSC, pH 7.0 (45° C.), followed by one 5-min wash in 2×SSC (45° C.) and one 5-min wash in 2×SSC with 1% Triton-X-100 (45° C.) and then blown dry. Fifty-µl reaction drops containing 5 µl DNA polymerase, e.g. Thermo Sequenase DNA Polymerase, 5 µl Thermo Sequenase reaction buffer (Amersham, Arlington Heights, Ill.), 200 µM of each dATP, dTTP, dCTP, and dGTP, and 5 µM AUAP primer are placed on an unfrosted microscope slide; the coverslip is inverted and gently placed on the slide so that the cells are in contact with the solution. Rubber cement or other suitable sealant is used to seal the coverslip to the microscope slide.

A suitable thermal profile consists of 95° C. for 10 min and 6 cycles of 94° C. for 2 min, 56° C. for 5 min, 56° C. for 5 min and a 5 min incubation at 72° C., and held at 4° C. until removed. Once complete, the coverslips are removed from the slide and soaked in a 4×SSC/0.1% triton-X-100 solution for 5 min at room temperature.

The regions of interest are scratched from the coverslip and placed in 0.2 ml microcentrifuge tubes. Fifty cycles are performed in 15 µl volumes containing 20 nM AUAP, 1.5 µl Thermo Sequenase DNA Polymerase, 1.5 µl Thermo Sequenase reaction buffer, 200 µM of each dATP, dGTP, dCTP, and dGTP. A suitable thermal profile is chosen to maximize DNA amplification, e.g. 95° for 10 min, 50 cycles of 94° C. for 1 min, 56° C. for 1 min, and 72° C. for 3 min, followed by a single 72° C. for 5 min and held at 4° C. until removed. PCR products are cloned into standard TA cloning vectors and the products are used for transfection.

Using this technique, cDNA fragments from various chromosomal regions may be isolated. The recovered sequences are cloned into plasmids. The plasmids may be amplified in bacterial hosts. Bacterial colonies may be picked for the different chromosomal regions. The clones are sequenced and the resulting sequences are matched using homology to currently know gene sequences. Microdissected cDNA sequence homology may be compared with the Non-redundant and "Expressed Sequence Tagged Site" (EST) databases at NCBI's web address, ncbi.nlm.nih.gov using Blast algorithms. Data from mapping of the human and rat genes can be further compared using NCBI's Homology Mapping web sites ncbi.nlm.nih.gov/Homology and ratmap.gen.gu.se. The putative function is based on protein-to-protein comparisons of the translated cDNA against the Non-redundant database. When the ESTs shown have no identifiable protein homology, this indicates the possibility of newly discovered genes.

Once the sequence data are known, these cDNA libraries can be arrayed on chips and used to assay the presence, absence and expression levels of genes from these chromosomal regions in other tumors. Some chromosomes such as rat chromosomes 2 and 3 are relatively easy to distinguish in an unbanded karyotype. To dissect the other less easily-distinguished chromosomes, chromosome band-specific DNA probes for regions that are outside of the desired area as designated by the CGH results are made. These band-specific probes are co-hybridized with the cDNA libraries and detected with a detection agent, e.g. horseradish peroxidase, a precipitate that is visible under normal bright-field microscopy. This permits the dissection of regions of interest rapidly and efficiently without compromising the quality of the resulting cDNA library.

5 Comparative Genomic Hybridization (CGH).

a. Microdissection

Microdissection is a technique in which a micromanipulator and a glass needle are used to selectively remove from a slide a small group of cells, a single cell, a chromosome or chromosome region. Using degenerate oligonucleotide priming (DOP) as indicated above, the entire DNA complement of a microdissected cell or chromosome can be amplified thousands of times. This technique is useful to generate chromosome-specific and region-specific DNA painting probes for use in fluorescence in situ hybridization (FISH) as described above.

Microdissection can also been used to remove small numbers of cells from formalin-fixed, paraffin-embedded tumors for further analysis and characterization.

The principal difficulty with microdissection lies in the number of cells, chromosomes or chromosome regions required for use as a PCR template. In chromosome microdissection, as many as 50 copies of a chromosome have typically been dissected and pooled to serve as a PCR template. Although attempts have been made to decrease the sample size to the optimal quantity of one, as far as the inventors are aware, no one has consistently demonstrated that this is possible. When obtaining samples of DNA from tumor sections for CGH analysis, if small numbers of cells could be analyzed rather than hundreds or thousands, the accuracy and precision of CGH would be greatly increased.

b. Improvement of CGH with Chromosomal DNA Amplification In Situ

CGH was first used in 1992 to detect chromosome alterations in breast tumors, and has been used since to analyze the karyotypes of many types of cancer. CGH uses DNA isolated from tumor cells labeled with a fluorochrome of one color (e.g., green), and DNA from normal cells, usually but not necessarily from a non-neoplastic region adjacent to the tumor, labeled with a different color (e.g., red). The tumor and normal DNA are pooled and hybridized to normal metaphase cells obtained from peripheral lymphocytes. Only the DNA from the tumor cells must be obtained from the tissue of interest; normal DNA and metaphase cells can come from any source from the selected species. Gains and losses of genetic material from the tumor are seen as changes in the ratio of red to green fluorescence. Regions in which the tumor has gained DNA, as might occur in the case of an oncogene, have more green than red fluorescence. If the tumor has lost DNA, which could be indicative of a region containing a tumor suppressor gene, there is more red fluorescence. While this technique cannot be used to identify chromosome exchanges such as translocations and inversions, it can readily detect overall gains and losses of genetic material within a group of cells, and has been used to produce a substantial amount of data on solid tumors. Representative CGH profiles are illustrated in FIG. 3.

Figure 3:
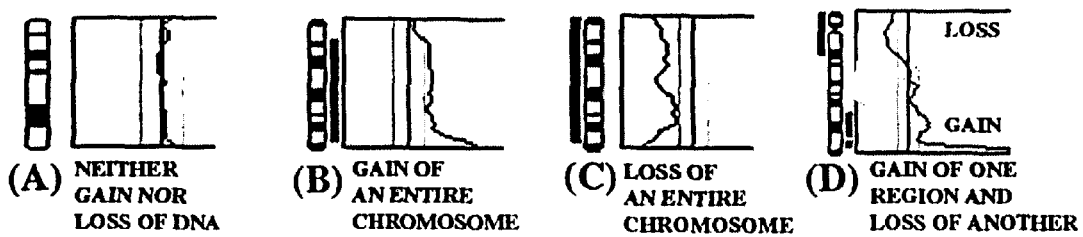
FIG. 3 shows examples of CGH profiles on 4 different rat chromosomes.

FIG. 3 illustrates examples of CGH profiles on 4 different rat chromosomes. Each chromosome is represented by an ideogram showing the banding pattern produced by the counterstain. Each CGH profile consists of a dark central vertical line representing a green:red ratio of one, lighter vertical lines on either side of it represent green:red ratios which, if exceeded, denote either a gain or a loss, respectively, and a wavy line that depicts the actual green:red profile. Panel A shows a chromosome that is present in its normal diploid number in the tumor. Panel B shows a chromosome that is present in increased number in the tumor, and Panel C shows a chromosome that has been lost by the tumor. The chromosome shown in Panel D contains one region that is present in excess and another region that has been lost.

Tumor heterogeneity presents a problem for CGH, however. A sample from a solid tumor may contain DNA from several different subclasses or subpopulations of cancerous cells, each descended from a single cell and possibly containing a different set of cytogenetic abnormalities. If the original cell in a population possessed certain genetic aberrations, all of its daughter cells should possess those aberrations as well. Since a cytogenetic hallmark of malignancy is the presence of a clonal population with substantial chromosome changes, it is very important when making a diagnosis to determine if such populations exist. However, if multiple clonal populations are sampled simultaneously, many chromosomal changes can be missed as a result of the mixing and concomitant dilution of small clones of abnormal cells. Any bias in the DNA sample, whether by mixing clonal populations of tumor cells or mixing tumor cells with normal cells, may substantially diminish the accuracy of the analysis. While is has been shown that CGH is tremendously useful in the analysis of solid tumors, it must be coupled with an extremely accurate means of tissue and cell sampling to be utilized to its fullest potential. Alternatively the need for such accurate sampling can be reduced where the amount of DNA associated with each chromosome is increased prior to microdissection. As such, in situ hybridization wherein the amount of DNA associated with the chromosomes is increased prior to performing CGH can greatly facilitate analysis.

c. CGH Analysis of Tumors.

CGH studies may be performed on tumors. The tumors may be benign or malignant. Carcinogenic agents such as heterocyclic amines may induce such tumors. Prior to performing CGH, the tumor DNA may be amplified in situ by the procedures outlined above.

Data from multiple carcinomas are pooled to identify chromosomal regions that are consistently gained or lost.

The in situ amplification procedure uses portions of solid tumors embedded in paraffin from which thin ($5\mu$ to $15\mu$ thin slices prepared with a microtome) are placed onto glass microscope slides, which is a standard method for histopathological diagnosis. Cells are dissected from the centers and edges of these tumor slices to determine the karyotype variation related to tumor progression. For example, one may dissect five small groups of cells from the center of each tumor. Five groups of cells may also be taken from the edge of each tumor, and five groups may be taken from a point midway between the center and the edge. Analyzing cells from the centers and edges of each tumor permits an evaluation of the development of numerical chromosome changes which accompany tumor growth, which is considered to be a hallmark of malignant progression.

The ability to perform CGH using in situ amplified DNA from cells microdissected from tissue sections offers numerous advantages. The primary concern with the prior techniques is that, as a result of the microtome slicing process, not all of the cells in a section will have complete nuclei. If partial nuclei are dissected and analyzed, the results will give an inaccurate picture of the cells' chromosome constitution. As such, by increasing the amount of DNA associated with the chromosomes prior to microdissection by DNA amplification in situ, the sensitivity of CGH analysis is increased.

5. Uses of the Techniques of the Invention

The techniques described herein find use in the study of chromosomes and chromosomal DNA gene expression and analysis.

In but one non limiting example, the techniques described herein find use in the study of cancer. Epidemiological evidence suggests that many cancers are related to the diet. High on the list of foods implicated in diet-related cancer is fried meat. In the past 20 years, heterocyclic amine carcinogens (HACs) have been identified as a class of compounds formed when meat is cooked at high temperatures. These compounds are genotoxic in bacteria and mammalian cells. Numerous short-term tests in animals have verified their activity in vivo, and long-term animal studies have established their carcinogenic activity. In spite of many significant advances, our knowledge of food-related carcinogenesis remains deficient for several reasons. First, the metabolic processes involved in converting inactive heterocyclic amine "parent" compounds to the active metabolite(s) are still not completely understood. Second, the tumors induced in most animal studies are frequently heterogeneous in origin due to the relatively high background rate of "spontaneous" cancers, which makes it difficult to determine the genes involved in HA-induced tumorigenesis. While heterocyclic amines are suspected to play a large role in breast carcinogenesis, little information exists as to their mechanism of action. One reason for this lack of data is that it is difficult to know whether a given tumor was actually induced by a specific agent, or was spontaneous in nature. For this reason, no consistent inter-tumor comparisons have yet been made. Consequently, little is known about the effects upon humans of chronic exposure to food-related carcinogens in specific target tissues.

The techniques of this invention permit an investigation of the molecular mechanisms of HA-induced mammary carcinogenesis. In particular, the techniques of this invention permit the location of regions of gain/loss in DNA from mammary tumors induced by the HACs, PhIP, MeIQx, IQ, and MeIQ. DNA is extracted from tumors known to be induced by these heterocyclic amine carcinogens, and chromosome regions gained, lost or amplified in the tumors are identified using comparative genomic hybridization (CGH).

Furthermore, the techniques of this invention permit a determination of the genes which are expressed in the chromosomal regions in normal mammary tissue, and a determination which of those genes are lost, amplified or mutated in the same chromosomal regions in mammary tumors. To perform this analysis, normal cDNA libraries are hybridized to normal metaphase cells as described herein. Chromosome regions of these metaphase cells that are identified to be involved in HA-induced tumorigenesis are analyzed, the recovered genes are sequenced and the genes are arrayed on microarrays. Messenger RNAs isolated from each tumor are then hybridized to the microarrays to determine which genes appear over- or under-expressed. Genes that are amplified or lost are sequenced to identify potential mutations that change DNA consensus sequences as well as protein coding regions that play an important role in HAC-induced tumorigenesis.

The techniques of this invention permit an analysis of the progression of genetic changes in tumors, including mammary tumors. Tumors are embedded in paraffin sections and DNA amplification is performed in situ. Next, small groups of cells are microdissected from paraffin-embedded tumor sections. Next, CGH is performed on DNA isolated from these cells, and these data are compared with CGH results obtained from total tumor DNA. The presence or absence of specific gene deletions and mutations are compared using PCR and microarray analysis on DNA obtained from tumor sections. By analyzing cells at increasing distances from the center of tumors one can analyze and characterize the cellular events that drive tumor progression.

The invention having been fully described is now exemplified by the following non-limiting examples.

EXAMPLES

Example 1

Cell and Chromosome Fixation In situ

Whole blood was cultured as previously described (Tucker, et al, Environ Mol Mutagen 30(3): 264–272 1997; Johnson et al., Mutagenesis 13(3) 217–27 1998). At 48 h after culturing, Colcemid (Gibco BRL, Indianapolis, Ind.) was added to a final concentration of 0.1 µg/ml. The cultures were harvested 4 h later by treatment with hypotonic solution (0.075 M KCl) for 30 min at 37° C. followed by three fixations in methanol:acetic acid (3:1 v/v). The fixed cells were dropped onto 24×60 mm coverslips, air dried and stored at room temperature.

Example 2

Chromosomal DNA Amplification In situ

Fifty-µl reaction drops containing 5 µl Thermo Sequenase DNA Polymerase, 5 µl Thermo Sequenase reaction buffer (Amersham, Arlington Heights, Ill.), 200 µM of each dATP, DTTP, dCTP, dGTP, and 40 µM tetramethylrhodamine-6-dUTP (Boehringer Mannheim, Indianapolis, Ind.), and 4 µM DOP primer (5'-CCGACTCGAGNNNNNNATGTGG-3') SEQ ID NO:1 were placed on unfrosted microscope slides; a coverslip prepared as in Example 1 was inverted and gently placed on the slide so that the cells were in contact with the solution. Rubber cement was used to seal the coverslip to the microscope slide. All PCR reactions were performed using a DNA Engine thermocycler (MJR Research Inc., Watertown, Mass.). The thermal profile consisted of 95° C. for 10 min, 8 cycles at 94° C. for 1 min, 30° C. for 5 min, and a ramp of 0.1° C./s up to 65° C. for 5 min, 12 cycles at 94° C. for 1 min, 56° C. for 5 min, and 72° C. for 5 min, followed by 72° C. for 5 min and held at 4° C. until removed. Once complete, the coverslips were removed from the slide and soaked in a 4×SSC/0.1% triton solution for 5 min at room temperature.

The fluorochrome labeled coverslip was then mounted onto a microscope slide using 0.1 µg/ml of 4',6-diamidino-2-phenylindole (DAPI) and an antifade solution. Metaphase spreads were visualized using a Zeiss Axioskop (Carl Zeiss, Inc, Thornwood, N.Y.) and images captured by a Vysis QUIPS Imaging Analysis System (Vysis, Downers Grove, Ill.). The PCR was considered successful if all chromosomes in a metaphase spread were labeled with the fluorochrome. The amplification showed brightly labeled chromosomes. The localization of fluorescence around each chromosome indicates that DNA was amplified during the PCR in situ reaction.

Example 3

Chromosomal DNA Amplification In situ For Production of Chromosome Painting Probes: HeadStart Microdissection 1. Methods and Materials Two coverslips were used for DOP-PCR in situ; one was used as a positive control by incorporating rhodamine-6-dUTP and the other was used for microdissection. Fifty-µl reaction drops containing 5 µl Thermo Sequenase DNA Polymerase, 5 µl Thermo Sequenase reaction buffer (Amersham, Arlington Heights, Ill.), 200 µM of each dATP, dTTP, dCTP, and dGTP (Boehringer Mannheim, Indianapolis, Ind.), and 4 µM DOP primer (5'-CCGACTCGAGNNNNNNATGTGG-3') SEQ ID NO:1 were placed on unfrosted microscope slides; a coverslip with fixed cells from Example 1 was inverted and gently placed on the slide so that the cells were in contact with the solution. Rubber cement was used to seal the coverslip to the microscope slide. Control DOP-PCR in situ experiments included 40 µM tetramethylrhodamine-6-dUTP added to the reaction in addition to the components listed above. All PCR reactions were performed using a DNA Engine thermocycler (MJR Research Inc., Watertown, Mass.). The thermal profile consisted of 95° C. for 10 min, 8 cycles at 94° C. for 1 min, 30° C. for 5 min, and a ramp of 0.1° C./s up to 65° C. for 5 min, 12 cycles at 94° C. for 1 min, 56° C. for 5 min, and 72° C. for 5 min, followed by 72° C. for 5 min and held at 4° C. until removed. ThermoSequenase was used because of its stability at high temperatures; new polymerase need not be added following each cycle.

Once complete, the coverslips were removed from the slide and soaked in a 4×SSC/0.1% triton solution for 5 min at room temperature. The fluorochrome labeled coverslip was then mounted onto a microscope slide using 0.1 µg/ml of 4',6-diamidino-2-phenylindole (DAPI) and an antifade solution. Metaphase spreads were visualized using a Zeiss Axioskop (Carl Zeiss, Inc, Thornwood, N.Y.) and images captured by a Vysis QUIPS Imaging Analysis System (Vysis, Downers Grove, Ill.). The PCR was considered successful if all chromosomes in a metaphase spread were labeled with the fluorochrome.

The unlabeled coverslip was removed from the SSC solution, blown dry, and used for microdissection. Appropriately sized glass needles were made using a Flaming/Brown Micropipette Puller (Sutter Instrument Co., Novato, Calif.). Using a Nikon Phase Contrast Microscope (Nikon Instruments Co., Melville, N.Y.) and a Narashige micromanipulator, one copy of the desired chromosome, arm or region was scraped and placed in a 500 µl microfuge tube. The DNA was then amplified by PCR in a 15 µl reaction drop containing 1.5 µl Thermo Sequenase DNA Polymerase, 1.5 µl Thermo Sequenase reaction buffer, 200 µM of each dATP, dGTP, dCTP, and dGTP, and 4 µM DOP primer. Thirty µl of mineral oil were added to the reaction mixture to prevent evaporation. The thermal profile consisted of 95° C. for 10 min, 6 cycles of 94° C. for 1 min, 30° C. for 2 min, and a ramp of 1° C./s up to 65° C. for 3 min, 30 cycles of 94° C. for 1 min, 56° C. for 1 min, and 72° C. for 3 min, followed by a single 72° C. for 5 min and held at 4° C. until removed. To verify that DNA amplification had occurred, each sample was electrophoresed on a 1.5% agarose gel at 100 V for 1 h. If appropriately-sized products (300–600 base pairs) were identified, a fluorochrome was incorporated in a second generation PCR using 2 µl of the first generation product as a template. The 50 µl labeling reaction contained 20 U Thermo Sequenase DNA Polymerase, 26 mM Tris-HCl, pH 9.0, 6.5 mM MgCl$_2$, 200 µM of each dATP, dTTP, dCTP, and dGTP, 40 µM Rhodamine-6-dUTP, and 4 µM DOP primer (5'-CCGACTCGAGNNNNNNATGTGG-3'). The thermal profile consisted of 95° C. for 5 min, 25 cycles at 94° C. for 1 min, 56° C. for 1 min, and 72° C. for 3 min, followed by 72° C. for 5 min and held at 4° C. until removed.

The painting probe was added to a hybridization mix (50% formamide, 2×SSC, 10% dextran sulfate, and 3 µg of blocking DNA) to a final volume of 15 µl. In the case of the rat, total genomic DNA was used as the blocking DNA, and CoT-1 DNA (Gibco BRL, Gaithersburg, Md.) was used for the human hybridizations. Metaphase spreads were denatured in 70% formamide/2×SSC, pH 7.0 for 3 min followed by successive washes in 70%, 85% and 100% ethanol for 3 min each. The probe mixture was denatured at 70° C. for 5 min and applied to the denatured slides, covered with 22×22 mm coverslips, sealed with rubber cement and hybridized overnight at 37° C. in a 5% $CO_2$ atmosphere.

Following hybridization. unbound probe was removed with three 5-min washes in 50% formamide, 2×SSC, pH 7.0 (45° C.), followed by one 5-min wash in 2×SSC (45° C.) and one 5-min wash in 2×SSC with 1% Triton-X (45° C.). The metaphase chromosomes were then counterstained with DAPI and an antifade solution. Metaphase spreads were observed using a Zeiss Axioskop fluorescence microscope with a dual band-pass filter for Rhodamine and DAPI (Chroma Technology Corp, Brattleboro, Vt.) and images captured by a Vysis QUIPS Imaging Analysis System (Vysis, Downers Grove, Ill.).

2. Results

PCR in situ amplifications performed with rhodamine-dUTP but without primers showed little or no fluorescence associated with the chromosomes, whereas PCR in situ amplification performed with primers plus rhodamine-dUTP showed brightly labeled chromosomes. The localization of fluorescence around each chromosome indicates that DNA is being amplified during the PCR in situ reaction, and that the nascent DNA remains associated with the chromosomes. The initial 8 cycles at a low annealing temperature were performed to produce DNA copies of the template that were properly sized for FISH (300–600 base pairs), with the DOP primer on both ends. The 12 high annealing temperature cycles were done to amplify exponentially the DNA fragments produced in the initial cycles.

Our primary concern with this technique was that the DNA products of the PCR in situ reaction would not remain closely associated with the regions from which they were replicated. As is known in the art, this phenomenon is seen when doing many cycles of PCR in situ, wherein the PCR products diffuse away from the chromosomal region from which they were derived. The effect increases gradually with successive PCR cycles and is generally quite severe after 20 cycles. This is a significant problem when attempting to localize a specific signal on a chromosome. Our initial efforts consisted of making WCPs for a variety of chromosomes, both human and rat, to ensure that only the desired chromosomes were labeled in subsequent FISH reactions. Results from analysis of WCPs for human chromosome 1 and rat chromosome 1, respectively, each made from a single chromosome on which DOP-PCR in situ had been performed prior to microdissection indicated that none of the probes cross-hybridized with any other chromosomes. We also dissected and pooled 2, 4, and 6 copies of human chromosome 1 on which PCR in situ had been performed; each of the dissections produced probe, and there was no visible difference in probe coverage or intensity among the three products. None of the three probes differed from the probe made from a single chromosome in either intensity or coverage. Pooling chromosomes, as is usually done when microdissecting, is unnecessary using HeadStart microdissection.

We then attempted to determine the extent of product diffusion along the length of individual chromosomes. To accomplish this, we first made CAPs for various chromosomes to see if the probes labeled only single arms in the FISH reactions and determined that there was sufficient resolution to produce arm-specific paints, we then dissected a single copy of human chromosome 2 in four contiguous pieces. The results indicated that that diffusion of the DOP-PCR in situ products does not present a significant problem when dissecting regions adjacent to one another. It is possible, however, that product drift would present a problem for microdissection in situ if too many PCR cycles were done.

As a control experiment, microdissection followed by DOP-PCR was performed on 3 single chromosomes that had not been subjected to PCR in situ prior to dissection. None of the three dissected chromosomes produced a visible probe (data not shown). In contrast, the success rate of HeadStart microdissection using single dissected chromosomes is approximately 90%.

Recently, work by Engelen [Engelen, J J, Albrechts J C, Hamers G J and Geraedts J P (1998)]. J Med Genet 35(4): 265–8.] showed that hydrating chromosomes immediately prior to dissection makes them easier to lift off the coverslip in one piece, rather than in fragments. This may result in greater chromatin recovery from each dissected chromosome, which would mean that fewer chromosomes would need to be dissected. Since the chromosomes become hydrated during the in situ PCR (but not, interestingly, any easier to lift off of the coverslip), we wanted to be sure that the increased efficiency of HeadStart microdissection was the result of DNA amplification, rather than simply hydration.

We tested this by performing parallel dissections on two coverslips, immediately following PCR in situ. The same cycling protocol was done on both coverslips, but one of the reactions was done without primers. Fluorescent controls showed that rhodamine-6-dUTP had been incorporated in the reaction in which primers were present, but not in the primerless reaction. Three single copies of human chromosome 1 were dissected from each of the two coverslips and put into separate microfuge tubes, and all 6 were subjected to DOP-PCR. Each of the 3 chromosomes dissected from the coverslip with the primer-containing PCR produced smooth paints that completely labeled chromosome 1. None of the three probes made from the primeness coverslip produced complete paints, and only one labeled the target chromosomes at all. This paint was very spotty in appearance and could not be used to score aberrations.

3. Discussion

Numerous papers have been published demonstrating new techniques intended to make microdissection more rapid and efficient. Through the use of new enzymes and better preparative methods, microdissection has become a widely used tool in cytogenetics. However, with one exception [(Guan, X Y, Trent J M and Meltzer P S (1993). Hum Mol Genet 2(8): 1117–21.)], researchers have found it necessary to dissect multiple copies of a target to produce quality probes.

There are several possible reasons why multiple chromosomes need to be dissected to make a library complex enough to be used for FISH. One reason is that it can be difficult to dissect an entire chromosome, and be sure that all of the chromatin has been successfully transferred into a microfuge tube. Secondly, even if the entire chromosome is successfully transferred, the amount of DNA involved is very small. Slight preferences in primer annealing during the initial low-temperature PCR could produce substantial asymmetries during amplification, resulting in incomplete probe coverage. Engelen, et al (1998) were able to improve the efficiency of chromatin removal from the coverslip by hydrating the chromosomes prior to dissection. This additional step made the chromosomes easier to remove, presumably resulting in more complete transfer to the microfuge tube. However, even with this modification, multiple copies of the target chromosomes were dissected to produce the paints. HeadStart microdissection is unique in consistently allowing probes to be made from single dissected chromosomes. This procedure differs from the frequently used procedure developed by Guan (1993), in that the DOP-PCR is performed on the coverslip prior to dissection, may then again be performed in the microfuge tube following dissection. We believe that the PCR in situ increases the amount of DNA being added to the microfuge tube following dissection; further amplification in the tube then produces a more complex probe than would be possible if a single, unamplified chromosome were dissected.

The ability to create complex painting probes from single chromosome fragments has considerable utility in a variety of areas. One major advantage of HeadStart microdissection is a substantial decrease in the time required for dissection, reducing the cost of producing probes. The potential for contamination with foreign DNA is also reduced, since the microfuge tube only needs to be opened once.

This technique also makes it easier to produce FISH painting probes from targets for which multiple dissections are difficult, if not impossible. Possible targets include marker and derivative chromosomes, clastogen-induced DNA breakpoints, the microchromosomes that are common in reptiles, amphibians and birds, and the smaller chromosomes in mammalian genomes that are difficult to differentiate, such as rodents and dogs. HeadStart microdissection will substantially increase the utility of microdissection, making an already powerful technique even more useful.

Example 4

Chromosomal DNA Amplification In Situ for Study of Carcinogenesis

1. Introduction

PhIP (2-amino-1-methyl-6-phenylimidazo [4,5-b] pyridine), a mutagen/carcinogen belonging to the class of heterocyclic amines (HCAs) found in cooked meats, is a mammary gland carcinogen in rats and has been implicated in the etiology of certain human cancers including breast cancer. To gain insight into the genomic alterations associated with PhIP-induced mammary gland carcinogenesis, we used DNA amplification in situ to produce a cDNA library coupled with comparative genomic hybridization (CGH) to examine chromosomal abnormalities in rat mammary carcinomas induced by PhIP, and for comparison, by DMBA (7, 12-dimethylbenz[a]anthracene), a potent experimental mammary carcinogen.

2. cDNA Library Manufacture

Rat mRNA was isolated from rat mammary tissue using the Ambion Poly(A)Pure mRNA isolation kit (Catalog #1915, Ambion Inc., Austin, Tex.). Human testis mRNA was purchased from Clontech Industries (Palo Alto, Calif.). First strand cDNA synthesis was done using the Amersham cDNA synthesis module (Catalog #RPN1256, Amersham Life Science, Buckinghamshire, England). The first strand primer was a modified version of the Life Technologies 3' RACE primer (Life Technologies, Rockville, Md.), with the addition of a random dATP, dGTP or dCTP on the 3' end to serve as an anchor SEQ ID NO:2. First strand synthesis time was cut to 15 minutes to provide a shorter library that was more amenable to hybridization. The sample was treated with RNase H per the Amersham kit, and a poly dC tail was added using terminal transferase (Roche, Indianapolis, Ind.). Twenty cycles of PCR were done using the Life Technologies Abridged Universal Amplification Primer (AUAP, 20 nM), 5 $\mu$l Thermo Sequenase DNA Polymerase, 5 $\mu$l Thermo Sequenase reaction buffer, 200 $\mu$M of each dATP, dGTP, dCTP, and dGTP in a 50 $\mu$l reaction volume. The thermal profile consisted of 95° C. for 10 min, 20 cycles of 94° C. for 1 min, 56° C. for 1 min, and 72° C. for 3 min, followed by a single 72° C. for 5 min and held at 4° C. until removed.

3. DOP-PCR In Situ

Fifty-$\mu$l reaction drops containing 5 $\mu$l Thermo Sequenase DNA Polymerase, 5 $\mu$l Thermo Sequenase reaction buffer (Amersham, Arlington Heights, Ill.), 200 $\mu$M of each dATP, dTTP, dCTP, and dGTP (Boehringer Mannheim, Indianapolis, Ind.), and 4 $\mu$M DOP primer (5'-CCGACTCGAGNNNNNNATGTGG-3') SEQ ID NO:1 were placed on unfrosted microscope slides; a coverslip prepared as in Example 1 was inverted and gently placed on the slide so that the cells were in contact with the solution. Rubber cement was used to seal the coverslip to the microscope slide. All PCR reactions were performed using a DNA Engine thermocycler (MJR Research Inc., Watertown, Mass.). The thermal profile consisted of 95° C. for 10 min, 8 cycles at 94° C. for 1 min, 30° C. for 5 min, and a ramp of 0.1° .C/s up to 65° C. for 5 min, 12 cycles at 94° C. for 1 min, 56° C. for 5 min, and 72° C. for 5 min, followed by 72° C. for 5 min and held at 4° C. until removed. Once complete, the coverslips were removed from the slide and soaked in a 4×SSC/0.1% triton solution for 5 min at room temperature.

4. cDNA In Situ Hybridization

Forty-$\mu$l reaction drops containing 50% formamide, 2×SSC, 10% dextran sulfate, 10 $\mu$g CoT-1 blocking DNA, and approximately 100 ng cDNA were added to the PCR in situ amplified coverslips, which were then placed on glass microscope slides and sealed with rubber cement. The rubber cement was allowed to dry, and then the slides were heated to 75° C. for 15 min to denature probe and target, and incubated for 48 h at 37° C. The slides were washed in 2×SSC for 15 min at 42° C., rinsed with distilled water and blown dry with nitrogen.

5. cDNA In Situ PCR

Fifty-$\mu$l reaction drops containing 5 $\mu$l Thermo Sequenase DNA Polymerase, 5 $\mu$l Thermo Sequenase reaction buffer (Amersham, Arlington Heights, Ill.), 200 $\mu$M of each dATP, DTTP, dCTP, and dGTP (Boehringer Mannheim, Indianapolis, Ind.), and 5 µM AUAP primer SEQ ID NO:3 were placed on an unfrosted microscope slide; the coverslip was inverted and gently placed on the slide so that the cells were in contact with the solution. Rubber cement was used to seal the coverslip to the microscope slide. The thermal profile consisted of 95° C. for 10 min and 6 cycles of 94° C. for 2 min, 56° C. for 5 min, 56° C. for 5 min and a 5 min incubation at 72° C., and held at 4° C. until removed. Once complete, the coverslips were removed from the slide and soaked in a 4×SSC/0.1% triton solution for 5 min at room temperature.

6. Post-Dissection Amplification

Fifty cycles of PCR were done in 15 µl volumes containing 20 nM AUAP, 1.5 µl Thermo Sequenase DNA Polymerase, 1.5 µl Thermo Sequenase reaction buffer, 200 µM of each dATP, dGTP, dCTP, and dGTP. The thermal profile consisted of 95° C. for 10 min, 50 cycles of 94° C. for 1 min, 56° C. for 1 min, and 72° C. for 3 min, followed by a single 72° C. for 5 min and held at 4° C. until removed.

7. Comparative Genomic Hybridization

The painting probe was added to a hybridization mix (50% formamide, 2×SSC, 10% dextran sulfate, and 3 µg of blocking DNA) to a final volume of 15 µl. Metaphase spreads were denatured in 70% formamide/2×SSC, pH 7.0 for 3 min followed by successive washes in 70%, 85% and 100% ethanol for 3 min each. The probe mixture was denatured at 70° C. for 5 min and applied to the denatured slides, covered with 22×22 mm coverslips, sealed with rubber cement and hybridized overnight at 37° C. in a 5% $CO_2$ atmosphere. Following hybridization. unbound probe was removed with three 5-min washes in 50% formamide, 2×SSC, pH 7.0 (45° C.), followed by one 5-min wash in 2×SSC (45° C.) and one 5-min wash in 2×SSC with 1% Triton-X (45° C.). The metaphase chromosomes were then counterstained with DAPI and an antifade solution. Metaphase spreads were observed using a Zeiss Axioskop fluorescence microscope and images were captured by a Vysis QUIPS Imaging Analysis System (Vysis, Downers Grove, Ill.).

8. CGH Analysis

To determine if accurate CGH was possible on these sections, we dissected approximately 20 normal female cells on which PCR in situ had been performed, and the DNA was amplified by DOP-PCR in microcentrifuge tubes. The resulting products were fluorescein-labeled by an additional PCR step. This probe was then co-hybridized with lissamine-labeled normal male rat DNA onto normal male rat metaphase spreads. Since the autosomes (non-sex chromosomes) are equally represented in male and female cells, they resulting balance of red and green label resulted in a yellow paint following hybridization. The green-labeled female DNA contained twice the X-chromosome DNA as the red-labeled male DNA did; as a result, the X chromosome was faintly green. There was no green-labeled Y-chromosome DNA in the female cells, so the Y-chromosome in the target metaphase was bright red. This demonstrated that DOP-PCR in situ followed by microdissection is an effective way to analyze the karyotypes of cells in paraffin-embedded tissue sections.

PhIP carcinomas were obtained from a previous study in which tumors were induced over a 25-week period after administration of PhIP (75 mg/kg, p.o., once per day, for 10-days) or DMBA (10 mg/kg, p.o., single dose) to 50-day old rats [Gracia, E., M. E. Ray, M. H. Polymeropoulos, A. Dehejia, P. S. Meltzer, and J. M. Trent, Isolation of chromosome-specific ESTs by microdissection-mediated cDNA capture. *Genome Res,* 7(2): p. 100–7 (1997)]. Vehicle control animals were run in parallel in both the PhIP and DMBA studies, and none of the control rats developed mammary carcinomas [Bonaldo, M. F., G. Lennon, and M. B. Soares, Normalization and subtraction: two approaches to facilitate gene discovery. *Genome Res,* 6(9): p. 791–806 (1996).]. This technique produces cancers only in animals treated with the specific agent, avoiding spontaneous tumors that can complicate analyses. We examined 9 different tubulopapillary carcinomas, 6 induced by PhIP and 3 induced by DMBA. All 9 of the carcinomas contained genomic changes detectable by CGH as either losses or gains/amplifications of chromosomal regions. All of the PhIP-induced carcinomas had five common regions of chromosome loss: short arms of chromosmomes 3, 11, 18 and the centromeric regions of chromosomes 2 and X. However, no common chromosomal abnormalities were observed among the DMBA-induced carcinomas, nor were there any common abnormalities between the DMBA- and the PhIP-induced cancers. The characteristic cytogenetic signature for PhIP-induced carcinomas made them clearly distinguishable from the carcinomas induced by DMBA. Besides the alterations in common, each PhIP-induced carcinoma also possessed unique alterations.

Since the resolution of CGH is ~10–15 megabases, clearly not all genetic alterations induced in these mammary carcinomas are likely to have been detected. However, the five common deletions which represent a signature pattern for PhIP-induced carcinomas indicate regions harboring genes that may play a role in PhIP-induced mammary carcinogenesis. Consistent with our CGH findings, PhIP-induced carcinomas also show a high frequency of allelic imbalance which is not observed in DMBA-induced carcinomas. As indicated by our data and results from other studies, multiple genetic alterations play a role in carcinogenesis [Hahn, W. C., C. M. Counter, A. S. Lundberg, R. L. Beijersbergen, M. W. Brooks, and R. A. Weinberg, Creation of human tumour cells with defined genetic elements. *Nature,* 400 (6743): p. 464–8 (1999).]. However, little is known about the genomic alterations associated with the development of rat mammary gland cancer by PhIP or other agents. The results suggest that the dietary carcinogen PhIP induces a cytogenetic signature that is distinct from the alterations induced by DMBA. The cytogenetic signature is akin to a DNA 'fingerprint', or characteristic mutation, which has been linked to several agents including PhIP and can be found in the genome of tumors arising after carcinogen exposure. The finding that characteristic cytogenetic alterations are induced in PhIP-induced mammary gland cancer has implications for ascertaining the genes associated with PhIP-induced rat mammary gland carcinogenesis, for bridging the genomic alterations in an experimental model with the genetic alterations associated with human disease, and for linking exposure to an environmental chemical carcinogen to a specific human cancer.

We performed the in situ amplifications and hybridized a human testis cDNA library to normal human metaphase chromosomes on which DOP-PCR in situ had been performed. Following hybridization, we amplified the bound probe with linker-specific PCR in situ and dissected the q-terminal band of human chromosome 2. After PCR amplification of the cDNA library using the linker primers, we used a primer set specific for the 3' end of the HHARP gene, which had been mapped to this region previously. We dissected 6 q-terminal fragments, amplified them separately, and were able to amplify the HHARP gene from each of them. As a control to check PCR product drift on the slides, the neighboring band was also dissected from each chromosome; the HHARP gene PCR products were not seen in any of these scrapes. This supported earlier results from Example 3, in which contiguous genomic DNA probes made following DOP-PCR in situ were shown to have little to no overlap.

We then performed GRM using a rat mammary tissue cDNA library, hybridized onto normal rat metaphase cells. Rather than analyze the deleted regions in the carcinomas, which would involve a significant sequencing effort, we focused on the rat chromosome 1 (RNO1) for our initial studies. RNO1 has known synteny to human chromosomes 5, 6 and 19 and mouse chromosome 7, all of which have been well characterized, making this an ideal test chromosome. We picked and sequenced (forward and reverse) 192 clones from a region spanning approximately RNO1p12–q21, and performed homology searches using the DataFoundry database storage and mining system [Critchlow, T., K. Fidelis, M. Ganesh, R. Musick, and T. Slezak, DataFoundry: information management for scientific data *IEEE Trans Inf Technol Biomed,* 4(1): p. 52–7 (2000).]; results are shown in Tables 1 and 2.

TABLE 1

Clones assigned a putative function based on homology

| Clone | Putative Function | BLAST Score |
|---|---|---|
| F12 | Translational tumor protein p21 | 97% ID |
| E09 | Type III collagen precursor | 30% ID |
| F07 | Serine/threonine kinase | 41% ID |

TABLE 2

Clones with only EST homology (100% match with existing rat EST sequences)

| Clone | Identifier | Blast Score |
|---|---|---|
| E04 | EST251684 | 652 Evalue 0.0 |
| E10 | EST204705 | 767 Evalue 0.0 |
| E11 | EST251684 | 317 Evalue 2.0E-84 |
| F03 | EST1749411 | 837 Evalue 0.0 |
| F10 | EST2418415 | 119 Evalue 1.0E-24 |
| F11 | EST2418415 | 180 Evalue 4.0E-43 |

Many of the hits were novel sequences; of those that had database homology to known genes, none had been mapped in the rat. However, many of the known genes that we sequenced have been mapped to syntenic regions in humans and mice, confirming the utility of GRM for recovering genes in selected chromosome regions.

The GRM technique provides a valuable link between the cytogenetic and physical mapping techniques that will quickly and reliably determine which genes are expressed in specific chromosomal regions of a particular tissue. Although the orthologous regions between rat and human have not been completely confirmed, it is notable that these deletions located on rat chromosomes 2, 3, 11, 18, and X are potentially orthologous to regions of human chromosomes 5q, 11p, 3p, 18q, and X, respectively, which harbor deletions (detected by LOH or CGH analysis) in certain human breast cancers [Tirkkonen, M., M. Tanner, R. Karhu, A. Kallioniemi, J. Isola, and O. P. Kallioniemi, Molecular cytogenetics of primary breast cancer by CGH. *Genes Chromosomes Cancer,* 21(3): p. 177–84 (1998), Ingvarsson, S., Molecular genetics of breast cancer progression. *Semin Cancer Biol,* 9(4): p. 277–88 (1999), Kerangueven, F., T. Noguchi, F. Coulier, F. Allione, V. Wargniez, J. Simony-Lafontaine, M. Longy, et al., Genome-wide search for loss of heterozygosity shows extensive genetic diversity of human breast carcinomas. *Cancer Res,* 57(24): p. 5469–74 (1997), Kerangueven, F., T. Noguchi, F. Coulier, F. Allione, V. Wargniez, J. Simony-Lafontaine, M. Longy, et al., Genome-wide search for loss of heterozygosity shows extensive genetic diversity of human breast carcinomas. *Cancer Res,* 57(24): p. 5469–74 (1997), Watanabe, T. K., M. T. Bihoreau, L. C. McCarthy, S. L. Kiguwa, H. Hishigaki, A. Tsuji, J. Browne, et al., A radiation hybrid map of the rat genome containing 5,255 markers. *Nat Genet,* 22(1): p. 27–36 (1999]. We anticipate that GRM will allow detailed genetic analysis of the genes located in the chromosomal regions which show characteristic deletions in PhIP mammary carcinomas and facilitate the comparison between rat and human mammary cancers through the combination of cytogenetic and genomic technology. This work should lead to understanding the underlying genetic changes inducing mammary cancer from dietary carcinogens.

Example 5

Isolation and Mapping of cDNAs

We constructed a cDNA library from mRNA obtained from normal rat mammary tissue and hybridized it to normal rat metaphase chromosomes.

1. cDNA Library Construction

Messenger RNA (mRNA) was isolated using the Ambion Poly(A)Pure mRNA isolation kit (Catalog #1915, Ambion Inc., Austin, Tex.). First strand cDNA synthesis was done using the Amersham cDNA synthesis module (Catalog #RPN1256, Amersham Life Science, Buckinghamshire, England). The first strand primer is a modified version of the Life Technologies (Life Technologies, Gaithersburg, Md.) 3' RACE (Rapid Amplification of cDNA Ends) primer, with the addition of a random dATP, dGTP or dCTP on the 3' end to serve as an anchor. First strand synthesis time was 1 hour for the 'full length' first strand to be used to make the 5'-rich library for protein homology screening, or is cut to 10 minutes to provide a shorter library comprised primarily of the 3' ends of the mRNA for EST screening. The samples were treated with RNase H per the Amersham kit, and a poly dC tail is added using terminal transferase (Roche, Indianapolis, Ind.). In the case of the shorter 3' library, 20 cycles of PCR are done using the Life Technologies Abridged Universal Amplification Primer (AUAP, 20 nM), 5 µl Thermo Sequenase DNA Polymerase, 5 µl Thermo Sequenase reaction buffer, 200 µM of each dATP, dGTP, dCTP, and dGTP in a 50 µl reaction volume. The thermal profile consists of 95° C. for 10 min, 20 cycles of 94° C. for 1 min, 56° C. for 1 min, and 72° C. for 3 min, followed by a single 72° C. for 5 min and incubation at 4° C. until removed.

To make the 5'-rich library, a second strand synthesis was done using the same reaction mixture as used in the 20-cycle PCR described above, but for one 10-minute extension. The entire process described above is then performed, starting with the poly dC tail addition, and followed by the 20 cycle PCR reaction using the AUAP primer. The result of this procedure is two cDNA libraries, one containing the 3' mRNA sequences and the other containing the 5' mRNA sequences. These two libraries are cohybridized for the GRM procedure, and result in a PCR-amplifiable product that covers the greatest possible amount of transcribed sequence.

2. Gene Recovery cDNA Microdissection

Fifty-µl reaction drops containing 5 µl Thermo Sequenase DNA Polymerase, 5 µl Thermo Sequenase reaction buffer (Amersham, Arlington Heights, Ill.), 200 µM of each dATP, dTTP, dCTP, and dGTP (Roche, Indianapolis, Ind.), and 4 µM DOP primer (5'-CCGACTCGAGNNNNNNATGTGG-3') are placed on unfrosted microscope slides; a coverslip prepared as in Example 1 was inverted and gently placed on the slide so that the cells were in contact with the solution. Rubber cement was used to seal the coverslip to the microscope slide. All PCR reactions are performed using a DNA Engine thermocycler (MJR Research Inc., Watertown, Mass.). The thermal profile consists of 95° C. for 10 min, 8 cycles at 94° C. for 1 min, 30° C. for 5 min, and a ramp of 0.1° C./s up to 65° C. for 5 min, 12 cycles at 94° C. for 1 min, 56° C. for 5 min, and 72° C. for 5 min, followed by 72° C. for 5 min and held at 4° C. until removed.

Once complete, the coverslips are removed from the slide and soaked in a 4×SSC/0.1% triton solution for 5 min at room temperature. The coverslips are then put into a 254 nm UV Stralinker (Stratagene, LaJolla, Calif.) for 15 minutes. This has no effect on hybridization, but greatly reduces the possibility of amplifying genomic DNA in addition to cDNA. Metaphase spreads on the coverslip are then denatured in 70% formamide/2×SSC, pH 7.0 for 3 min followed by successive washes in 70%, 85% and 100% ethanol for 3 min each. A 40 µl reaction mix containing 50% formamide, 2×SSC, 10% dextran Sulfate, 10 µg CoT-1 DNA, and 500 ng cDNA is denatured at 70° C. for 5 min and applied to a clean slide, covered with the denatured coverslips, sealed with rubber cement and hybridized overnight at 37° C. in a 5% CO$_2$ atmosphere. Following hybridization, unbound probe is removed with three 5-min washes in 50% formamide, 2×SSC, pH 7.0 (45° C.), followed by one 5-min wash in 2×SSC (45° C.) and one 5-min wash in 2×SSC with 1% Triton-X (45° C.) and then blown dry. Fifty-µl reaction drops containing 5 µl Thermo Sequenase DNA Polymerase, 5 µl Thermo Sequenase reaction buffer (Amersham, Arlington Heights, Ill.), 200 µM of each dATP, dTTP, dCTP, and dGTP (Boehringer Mannheim, Indianapolis, Ind.), and 5 µM AUAP primer are placed on an unfrosted microscope slide; the coverslip is inverted and gently placed on the slide so that the cells are in contact with the solution. Rubber cement is used to seal the coverslip to the microscope slide. The thermal profile consists of 95° C. for 10 min and 6 cycles of 94° C. for 2 min, 56° C. for 5 min, 56° C. for 5 min and a 5 min incubation at 72° C., and held at 4° C. until removed. Once complete, the coverslips are removed from the slide and soaked in a 4×SSC/0.1% triton solution for 5 min at room temperature.

The regions of interest are scratched from the coverslip and placed in 0.2 ml microcentrifuge tubes. Fifty cycles of PCR were done in 15 µl volumes containing 20 nM AUAP, 1.5 µl Thermo Sequenase DNA Polymerase, 1.5 µl Thermo Sequenase reaction buffer, 200 µM of each dATP, dGTP, dCTP, and dGTP. The thermal profile consisted of 95° C. for 10 min, 50 cycles of 94° C. for 1 min, 56° C. for 1 min, and 72° C. for 3 min, followed by a single 72° C. for 5 min and held at 4° C. until removed. PCR products are cloned into standard TA cloning vectors (Promega, Madison, Wis.), and the products are transfected.

Using a microdissector, the chromosome regions in the normal cells that correspond to regions missing in the tumor cells were isolated. Similar procedures have been published, but these lack the sensitivity to isolate single copy genes from normal metaphase chromosomes reliably. Most of the recovered sequences corresponded to genes that were greatly amplified in the tumor; the technique was not thought to be sensitive enough to recover single copy genes from normal chromosomes because as many as 50 fragments of the region of interest were required to obtain enough cDNA for subsequent PCR amplification, cloning, and sequencing. While this was possible using a morphologically distinct target such as an abnormal chromosome in a cancer cell, it is nearly impossible to dissect multiple copies of the same chromosome (or chromosome region) from normal metaphase cells, since the chromosomes cannot be banded following hybridization and many chromosomes are difficult to distinguish. We solved this problem by using PCR in situ prior to microdissection to amplify the target chromosomes prior to hybridizing the cDNA library. Following hybridization we then amplified the cDNA library in situ.

Using this technique, we isolated cDNA fragments from the proximal region of rat chromosome 2 and the short arm of rat chromosome 1. The recovered sequences were cloned into plasmids using a TA-cloning kit (Promega, Madison, Wis.). The cloning efficiency was greater than 80%; insert sizes ranged from 310 to 2000 bases, with an average insert length ~400 bp. We picked 46 colonies for each of the two regions, which were sequenced by our collaborators at the Joint Genome Institute and processed though PolyPhred-Phrap to remove vector sequence and build clone contigs. The files generated in PolyPhredPhrap are then batch fed through Blast at the website ncbi.nlm.nih.gov to find EST clones and non-redundant nucleic and protein sequences with high homology to human, mouse or known rat genes. Data from mapping of the rat and human genes can be further compared using NCBI's Homology Mapping web sites ncbi.nlm.nih.gov/Homology and ratmap.gen.gu.se.

This experiment produced several 100% matches, based on protein and DNA homology, to sequences from the rat.

Numerous other genes, both known and novel, were also sequenced. All of the initial Blast searches were done manually; subsequent searches were done using the DataFoundry search capabilities and produced similar results in a fraction of the time.

The identity of genes isolated from rat chromosomes 2 and 1 are shown in Tables 4, 5 and 6. Microdissected cDNA sequence homology is compared with the Non-redundant and the "Expressed Sequence Tagged Site" (EST) databases at NCBI http://www.ncbi.nlm.nih.gov using Blast algorithms. In Table 4, the putative function is based on protein-to-protein or DNA to DNA comparisons against the Non-redundant database. The percentage for protein homology is listed as the identity (ID). In Table 5, those ESTs with no identifiable protein homology are shown. All of these clones were found using both DataFoundry and manual searching. In Table 6, clones with unique sequence, but no amino acid or DNA homology are shown. Genes shown in Tables 5 and 6 may represent newly discovered mammalian genes.

TABLE 4

Clones assigned a putative function based on homology.

| Clone | Putative Function | Blast Score |
| --- | --- | --- |
| A06 | Cysteine-rich mbn protein | 68% ID |
| A03 | ADP/ATP carrier | 30% ID |
| A12 | Adenosine kinase | 321 Evalue 2.0E-85 |
| B03, B08 | Rat Ribosomal protein L23A | 100% ID |
| B04 | Occludin (ocln) | 196 Evalue 3.0E-48 |
| B09 | CDK 103 mRNA | 345 Evalue 2.0E-92 |
| B12 | Hypothetical protein ligase-like | 71% ID |
| E09 | Type III collagen precursor | 30% ID |
| F07 | Serine/threonine kinase | 41% ID |

TABLE 4-continued

Clones assigned a putative function based on homology.

| Clone | Putative Function | Blast Score |
| --- | --- | --- |
| F09, E08 F12. | Eif4a-rs-EST 1927790 Translational tumor protein p21 | 472 Evalue 1.0E-131 97% ID |

TABLE 5

Clones with only EST homology

| Clone | Identifier | Blast Score |
| --- | --- | --- |
| A07 | UI-R-C3-tp-c-06-0-UI.s1 | 521 Evalue 1.0E-145 |
| B10 | EST234223 | 68 Evalue 4.0E-09 |
| E04 | EST251684 | 652 Evalue 0.0 |
| E10 | EST204705 | 767 Evalue 0.0 |
| E11 | EST251684 | 317 Evalue 2.0E-84 |
| F03 | EST1749411 | 837 Evalue 0.0 |
| F10 | EST2418415 | 119 Evalue 1.0E-24 |
| F11 | EST2418415 | 180 Evalue 4.0E-43 |

TABLE 6

Unique clones with no known homology

| Clone | |
| --- | --- |
| A10 | H03 |
| A09 | H04 |
| B01 | G05 |
| C04 | G06 |
| E01 | F09 |

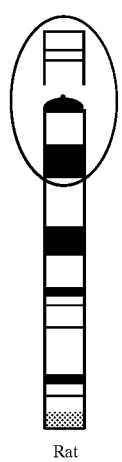

Rat chromosome 1.

Genes Mapped to Rat Chromosome 1. The oval shows the region of rat chromosome 1 that was microdissected. The sequenced clones were searched via nucleotide sequence and protein search engines sponsored by NIH, including BLAST and dBEST to find EST (Expressed Sequence Tag) clones and non-redundant nucleic and protein sequences with high homology to human, mouse or known rat genes. Searches were performed using the DataFoundry search engine. Data from mapping of the rat and human genes was further compared using NCBI's Homology Mapping web site www.ncbi.nlm.nih.gov/Homology/_and_http://ratmap.gen.gu.se/. Putative functions are based on homologies as shown. In addition, numerous other clones were unique, containing no known homologies.

CLONES ASSIGNED A PUTATIVE FUNCTION BASED ON HOMOLOGY

| Clone | Putative Function | BLAST Score |
| --- | --- | --- |
| F12 | Translational tumor protein p21 | 97% ID |
| E09 | Type III collagen precursor | 30% ID |
| F07 | Serine/threonine kinase | 41% ID |

Clones with only EST homology (100% match with existing rat EST sequence)

-continued

| Clone | Identifier | Blast Score |
|---|---|---|
| E04 | EST251684 | 652 Evalue 0.0 |
| E10 | EST204705 | 767 Evalue 0.0 |
| E11 | EST251684 | 317 Evalue 2.0E-84 |
| F03 | EST1749411 | 837 Evalue 0.0 |
| F10 | EST2418415 | 119 Evalue 1.0E-24 |
| F11 | EST2418415 | 180 Evalue 4.0E |

We claim:

1. A method of microdissecting chromosomes, comprising
   a) fixing cells on a surface wherein said cells comprise chromosomes and said chromosomes include DNA;
   b) amplifying said DNA on said surface; and
   c) after step b), microdissecting said chromosomes.

2. The method of claim 1 wherein said DNA is amplified by PCR in step b).

3. The method of claim 2 wherein said PCR is DOP-PCR.

4. The method of claim 1 wherein said surface is a microscope slide coverslip.

5. The method of claim 4 wherein said coverslip is affixed to a microscope slide containing PCR reaction buffer so that the cells are in contact with said reaction buffer.

6. The method of claim 5 wherein said coverslip is affixed to said slide with rubber cement.

7. A method of amplifying chromosomal DNA in situ, comprising:
   a) fixing cells on a surface wherein said cells comprise chromosomes and said chromosomes include DNA;
   b) preparing a PCR reaction buffer including DNA polymerase;
   c) combining said PCR reaction buffer with said fixed cells of step a);
   d) amplifying said DNA by PCR in situ; and
   e) after step d), microdissecting said chromosomes.

8. The method of claim 7 wherein said DNA is amplified by DOP-PCR in step d).

9. The method of claim 7 wherein said surface is a microscope cover slide.

10. A method of generating a chromosome region-specific nucleic acid for a chromosomal region of interest comprising the steps of:
    a) obtaining chromosomes containing chromosomal DNA;
    b) amplifying said chromosomal DNA in situ; and
    c) after step b), microdissecting said chromosome to provide a chromosome region-specific nucleic acid for a chromosome region of interest.

11. The method of claim 10 wherein step b) further comprises a polymerase chain reaction.

12. The method of claim 10 further comprising step d) labeling the amplified microdissected chromosomal DNA.

13. The method of claim 10 wherein step b) further comprises the steps of priming the amplification with a polynucleotide having the nucleotide sequence depicted in SEQ ID NO:1.

14. The method of claim 10 wherein the region of interest comprises a chromosome band.

15. The method of claim 10 wherein the chromosomal region of interest is translocated or otherwise relocated from its normal chromosomal location.

16. The method of claim 12 wherein the label is fluorescent.

17. The method of claim 12 wherein the label is biotin based or digoxigen-based.

18. The method of claim 10 wherein the nucleic acid is region-specific.

19. The method of claim 10 wherein said chromosomes of step a) are fixed to a surface.

20. The method of claim 19 wherein said surface is a microscope cover slip.

21. A method of localizing a chromosomal region of interest in a chromosome sample having nucleic acid sequences, comprising the steps of:
    a) providing a chromosome region-specific probe generated by:
       (i) amplifying the nucleic acid sequences of said chromosome in situ to provide an amplified chromosomal region of interest;
       (ii) after step (i), microdissecting the chromosomal region of interest to provide a microdissected chromosome fragment;
       (iii) amplifying the microdissected chromosome fragment; and
       (iv) labeling the amplified fragment to provide the probe; and
    b) contacting the chromosome sample with the probe under conditions favorable for hybridization between the probe and complementary nucleic acid sequences in the sample; and
    c) determining the existence and location of hybridization in the chromosome sample.

22. The method of claim 21 wherein amplification is by a polymerase chain reaction.

23. The method of claim 21 wherein the label is fluorescent.

24. The method of claim 21 wherein the sample comprises a DNA library.

25. A method of screening a library of nucleic acid clones for a clone of a chromosomal region of interest having nucleic acid sequences comprising the steps of:
    a) providing a chromosome region-specific probe generated by:
       (i) amplifying the nucleic acid sequences of said chromosome in situ to provide an amplified chromosomal region of interest;
       (ii) after step (i), microdissecting the chromosomal region of interest to provide a microdissected chromosome fragment;
       (iii) amplifying the microdissected chromosome fragment; and
       (iv) labeling the amplified fragment to provide the probe;
    b) providing the library of clones to be screened;
    c) contacting each clone with the probe under conditions favorable for nucleic acid hybridization; and
    d) determining whether and in which clone hybridization has occurred.

26. The method of claim 25 wherein said library is a genomic DNA library.

27. The method of claim 25 wherein said library is a cDNA library.

28. A method of amplifying a cDNA library, comprising:
   a) fixing cells on a surface wherein said cells comprise chromosomes and said chromosomes include genomic DNA;
   b) amplifying said genomic DNA on said surface to form amplified genomic DNA;
   c) hybridizing said cDNA library to said genomic DNA to form DNA hybrids;
   d) amplifying said DNA hybrids on said surface to form an amplified cDNA library; and
   e) after step d), microdissecting said chromosomes.

29. The method of claim 28 wherein said genomic DNA in step b) is amplified by PCR.

30. The method of claim 29 wherein said PCR is DOP-PCR.

31. The method of claim 28 wherein said DNA hybrid of step d) is amplified by PCR.

32. The method of claim 31 wherein said PCR includes the use of primers specific for said cDNA library.

33. The method of claim 28 including the additional step e) microdissecting said chromosomes wherein said chromosomes include the DNA hybrid from step c).

34. The method of claim 33 including the additional step f) amplifying said DNA hybrid from said microdissected chromosomes.

35. A method of preparing a cDNA library specific to a particular chromosome region, comprising:
   a) fixing chromosomes including said chromosome region on a surface wherein said chromosomes and said chromosome region include genomic DNA;
   b) amplifying said genomic DNA in situ to form amplified genomic DNA;
   c) hybridizing said cDNA library to said genomic DNA to form DNA hybrids;
   d) amplifying said DNA hybrids on said surface to form an amplified cDNA library;
   e) after step d), microdissecting said chromosome region wherein said chromosome region includes a portion of said amplified cDNA library; and
   f) amplifying said portion of said cDNA library.

36. The method of claim 35 wherein said DNA of step b) is amplified by PCR.

37. The method of claim 36 wherein said PCR is DOP-PCR.

38. The method of claim 35 wherein said DNA hybrids of step d) are amplified with primers specific for said cDNA library.

39. The method of claim 35 where said portion of said cDNA library of step f) is amplified with primers specific for said cDNA library.

40. The method of claim 35 including the additional step b-1) treating said amplified genomic DNA with UV light to form dimers in said genomic DNA.

41. A method of identifying expressed genes, comprising:
   a) fixing cells on a surface wherein said cells comprise chromosomes and said chromosomes include genomic DNA;
   b) amplifying said genomic DNA on said surface to form amplified genomic DNA;
   c) obtaining a cDNA library;
   d) hybridizing said cDNA library to said genomic DNA to form DNA hybrids;
   e) after step d), microdissecting said chromosomes;
   f) amplifying said DNA hybrids on said surface to form an amplified cDNA library; and
   g) analyzing said DNA hybrids to identify said expressed genes.

42. The method of claim 41 wherein said DNA in step b) is amplified by PCR.

43. The method of claim 42 wherein said PCR is DOP-PCR.

44. The method of claim 41 wherein said DNA hybrid of step f) is amplified by PCR.

45. The method of claim 44 wherein said PCR includes the use of primers specific for said cDNA library.

46. A method of identifying expressed genes, comprising:
   a) fixing cells on a surface wherein said cells comprise chromosomes and said chromosomes include genomic DNA;
   b) amplifying said genomic DNA on said surface to form amplified genomic DNA;
   c) obtaining a cDNA library;
   d) hybridizing said cDNA library to said genomic DNA to form DNA hybrids;
   e) amplifying said DNA hybrids on said surface to form an amplified cDNA library;
   f) after step e), microdissecting said chromosomes including said amplified cDNA library; and
   g) sequencing members of said amplified cDNA library to identify said expressed genes.

47. The method of claim 46 wherein said DNA of step b) is amplified by PCR.

48. The method of claim 47 wherein said PCR is DOP-PCR.

49. The method of claim 46 wherein said DNA hybrids of step e) are amplified with primers specific for said cDNA library.

50. The method of claim 46 where said portion of said cDNA library of step f) is amplified with primers specific for said cDNA library.

51. A method of identifying expressed genes, comprising:
   a) fixing cells on a surface wherein said cells comprise chromosomes and said chromosomes include genomic DNA;
   b) amplifying said genomic DNA on said surface to form amplified genomic DNA;
   c) obtaining a cDNA library;
   d) hybridizing said cDNA library to said genomic DNA to form DNA hybrids;
   e) amplifying said DNA hybrids on said surface to form an amplified cDNA library;
   f) after step e), microdissecting said chromosomes including said amplified cDNA library; and
   g) further amplifying said cDNA library to form a further amplified cDNA library; and
   h) sequencing members of said further amplified cDNA library to identify said expressed genes.

52. The method of claim 51 wherein said DNA of step b) is amplified by PCR.

53. The method of claim 52 wherein said PCR is DOP-PCR.

54. The method of claim 51 wherein said DNA hybrids of step e) are amplified with primers specific for said cDNA library.

55. The method of claim 51 where said portion of said cDNA library of step f) is amplified with primers specific for said cDNA library.

56. A method of amplifying chromosomal DNA in situ, comprising:
   a) providing cells embedded in paraffin wherein said cells comprise chromosomes and said chromosomes include DNA;
   b) preparing a PCR reaction buffer;
   c) combining said PCR reaction buffer with said paraffin embedded cells of step a);

57. The method of claim 56 wherein said DNA is amplified by DOP-PCR in step d).

58. The method of claim 56 wherein the cells are selected from mammalian, reptile, amphibian, avian and plant cells.

59. The method of claim 58 wherein said mammalian cells are human cells.

60. The method of claim 56 including the additional step e) microdissecting said chromosomes.

61. A method of normalizing a cDNA library, comprising:
   a) fixing cells on a surface wherein said cells comprise chromosomes and said chromosomes include genomic DNA;
   b) amplifying said genomic DNA on said surface to form amplified genomic DNA;
   c) hybridizing said cDNA library to said genomic DNA to form DNA hybrids;
   d) amplifying said DNA hybrids on said surface to form an amplified cDNA library;
   e) microdissecting said chromosomes including said amplified cDNA library; and
   f) amplifying said amplified cDNA library to form a normalized cDNA library.

62. The method of claim 61 wherein said DNA of step b) is amplified by PCR.

63. The method of claim 62 wherein said PCR is DOP-PCR.

64. The method of claim 61 wherein said DNA hybrids of step e) are amplified with primers specific for said cDNA library.

65. The method of claim 41 wherein said DNA hybrids are analyzed by DNA sequencing.

66. The method of claim 41 wherein said DNA hybrids are analyzed by gel electrophoresis.

67. The method of claim 61 wherein said DNA hybrids are amplified by DOP-PCR in step d).

68. The method of claim 61 wherein the cells are selected from mammalian, reptile, amphibian, avian and plant cells.

69. The method of claim 68 wherein said mammalian cells are human cells.

* * * * *

SEQUENCE LISTING

<160> NUMBER OF SEQ ID NOS: 5

<210> SEQ ID NO 1
<211> LENGTH: 22
<212> TYPE: DNA
<213> ORGANISM: Artificial Sequence
<220> FEATURE:
<223> OTHER INFORMATION: degenerate oligonucleotide primer (DOP)
<221> NAME/KEY: misc_feature
<222> LOCATION: (1)...(22)
<223> OTHER INFORMATION: n = A,T,C or G

<400> SEQUENCE: 1
ccgactcgag nnnnnnatgt gg                                            22

<210> SEQ ID NO 2
<211> LENGTH: 37
<212> TYPE: DNA
<213> ORGANISM: Artificial Sequence
<220> FEATURE:
<223> OTHER INFORMATION: synthetic construct

<400> SEQUENCE: 2
ggccacgcgt cgactagtac tttttttttt tttttta                            37

<210> SEQ ID NO 3
<211> LENGTH: 37
<212> TYPE: DNA
<213> ORGANISM: Artificial Sequence
<220> FEATURE:
<223> OTHER INFORMATION: synthetic construct

<400> SEQUENCE: 3
ggccacgcgt cgactagtac tttttttttt tttttc                             37

<210> SEQ ID NO 4
<211> LENGTH: 37
<212> TYPE: DNA
<213> ORGANISM: Artificial Sequence
<220> FEATURE:
<223> OTHER INFORMATION: synthetic construct

<400> SEQUENCE: 4
ggccacgcgt cgactagtac tttttttttt tttttg                             37

<210> SEQ ID NO 5
<211> LENGTH: 20
<212> TYPE: DNA
<213> ORGANISM: Artificial Sequence
<220> FEATURE:
<223> OTHER INFORMATION: Technologies Abriged Univerisal Amplification
      Primer

```
<400> SEQUENCE: 5
ggccacgcgt cgactagtac                                                    20
```